US009856197B2

(12) United States Patent
Zubrin et al.

(10) Patent No.: US 9,856,197 B2
(45) Date of Patent: Jan. 2, 2018

(54) SYSTEMS AND METHODS FOR MANUFACTURE OF DIMETHYL ETHER (DME) FROM NATURAL GAS AND FLARE GAS FEEDSTOCK

(71) Applicant: Pioneer Energy Inc., Lakewood, CO (US)

(72) Inventors: Robert M Zubrin, Golden, CO (US); Boris Nizamov, Highlands Ranch, CO (US); Thomas L Henshaw, Monument, CO (US); Adam M Kortan, Arvada, CO (US); James Siebarth, Lakewood, CO (US); Colin Apke, Castle Rock, CO (US); Mark Berggren, Golden, CO (US)

(73) Assignee: Pioneer Energy, Inc., Lakewood, CO (US)

( * ) Notice: Subject to any disclaimer, the term of this patent is extended or adjusted under 35 U.S.C. 154(b) by 0 days.

(21) Appl. No.: 15/447,050

(22) Filed: Mar. 1, 2017

(65) Prior Publication Data
US 2017/0174599 A1   Jun. 22, 2017

Related U.S. Application Data

(62) Division of application No. 14/953,268, filed on Nov. 27, 2015, now Pat. No. 9,643,906.
(Continued)

(51) Int. Cl.
*C07C 41/00* (2006.01)
*C07C 41/01* (2006.01)
(Continued)

(52) U.S. Cl.
CPC .............. *C07C 41/42* (2013.01); *C01B 3/36* (2013.01); *C01B 3/386* (2013.01); *C07C 41/09* (2013.01);
(Continued)

(58) Field of Classification Search
CPC .... C01B 3/00; C01B 3/02; C01B 3/32; C01B 3/34; C01B 3/36; C01B 3/38;
(Continued)

(56) References Cited

U.S. PATENT DOCUMENTS 7,739,875 B2 * 6/2010 Bartlett ..................... C01B 3/34
                                                   60/39.12
8,461,217 B2 * 6/2013 Olah ..................... C07C 29/151
                                                   518/700
(Continued)

OTHER PUBLICATIONS

M. S. Spencer, "The role of zinc oxide in Cu/ZnO catalysts for methanol synthesis and the water-gas shift reaction," Topics in Catalysis 8, pp. 259-266, 1999.

*Primary Examiner* — Natasha Young
(74) *Attorney, Agent, or Firm* — American Patent Agency PC; Daniar Hussain

(57) ABSTRACT

Disclosed is a method that reforms flare gas or other raw natural gas source, using air without steam, to directly produce dimethyl ether (DME), a direct diesel substitute. The method first reforms an air-natural gas mixture at ambient atmospheric pressures, and then compresses the resulting CO-hydrogen-nitrogen gas mixture to 100-2,000 psi, and feeds it through a combined reactor which reacts the gas mixture directly into DME. The nitrogen is returned to the atmosphere. DME is an excellent diesel fuel, and can be used to displace significantly costlier and dirtier petroleum-based diesel fuel, while solving a critical problem with flaring or other wasted natural gas. For example, the roughly 120 billion cubic feet per year that was flared in North Dakota in 2014 could be converted into over 3 million tons of DME using the disclosed method.

24 Claims, 14 Drawing Sheets

Related U.S. Application Data

(60) Provisional application No. 62/085,391, filed on Nov. 28, 2014.

(51) Int. Cl.

| | |
|---|---|
| *C07C 41/09* | (2006.01) |
| *C07C 41/34* | (2006.01) |
| *C07C 41/40* | (2006.01) |
| *C07C 41/42* | (2006.01) |
| *C01B 3/00* | (2006.01) |
| *C01B 3/02* | (2006.01) |
| *C01B 3/32* | (2006.01) |
| *C01B 3/34* | (2006.01) |
| *C01B 3/36* | (2006.01) |
| *C01B 3/38* | (2006.01) |

(52) U.S. Cl.
CPC .. *C01B 2203/0261* (2013.01); *C01B 2203/06* (2013.01); *C01B 2203/1241* (2013.01); *C01B 2203/1258* (2013.01)

(58) Field of Classification Search
CPC . C01B 3/386; C01B 2203/00; C01B 2203/02; C01B 2203/025; C01B 2203/0261; C01B 2203/06; C01B 2203/12–2203/1211; C01B 2203/1235; C01B 2203/1241; C01B 2203/1258; C07C 41/00; C07C 41/01; C07C 41/09; C07C 41/34; C07C 41/40; C07C 41/42
See application file for complete search history.

(56) References Cited

U.S. PATENT DOCUMENTS

| | | |
|---|---|---|
| 8,551,444 B2 | 10/2013 | Agnihotri et al. |
| 8,835,517 B2 | 9/2014 | Cheiky et al. |
| 2008/0033066 A1 | 2/2008 | Haynes |
| 2012/0103611 A1 | 5/2012 | Brandl et al. |
| 2013/0324622 A1* | 12/2013 | Cheiky ............... C07C 41/42 518/700 |

\* cited by examiner

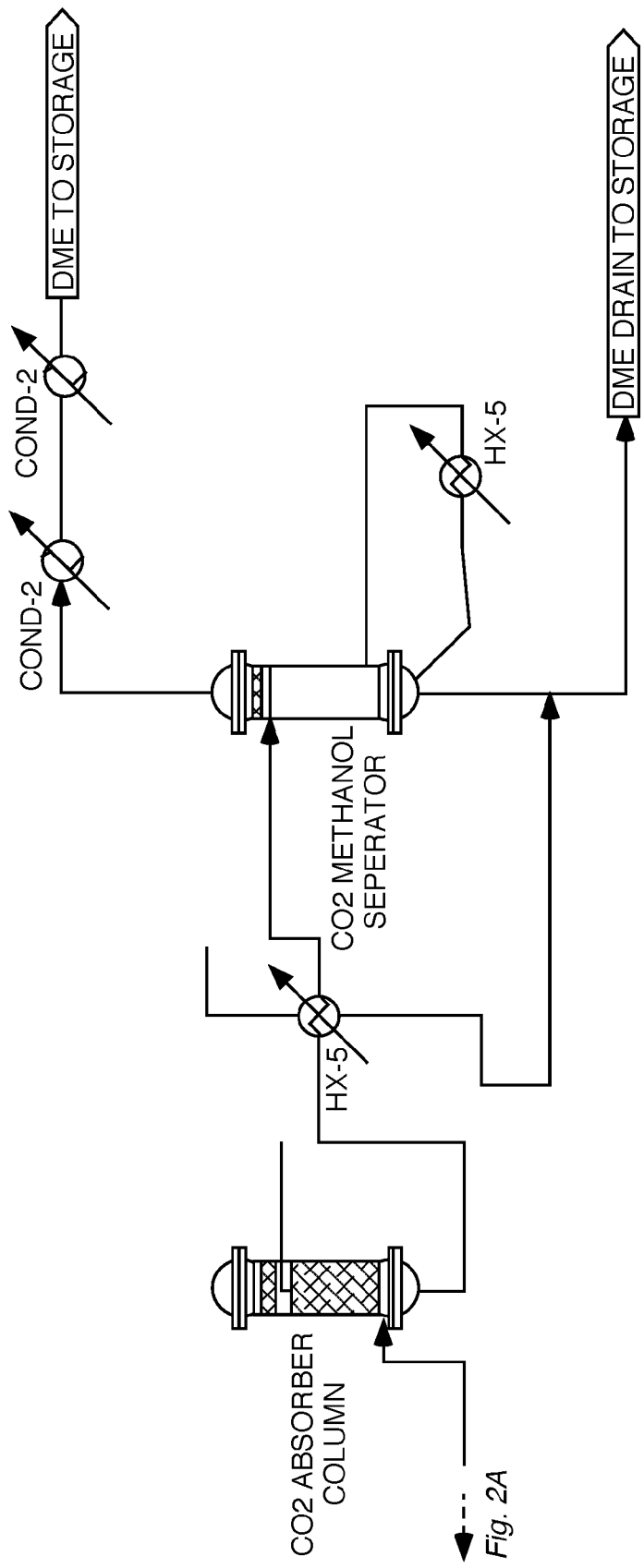

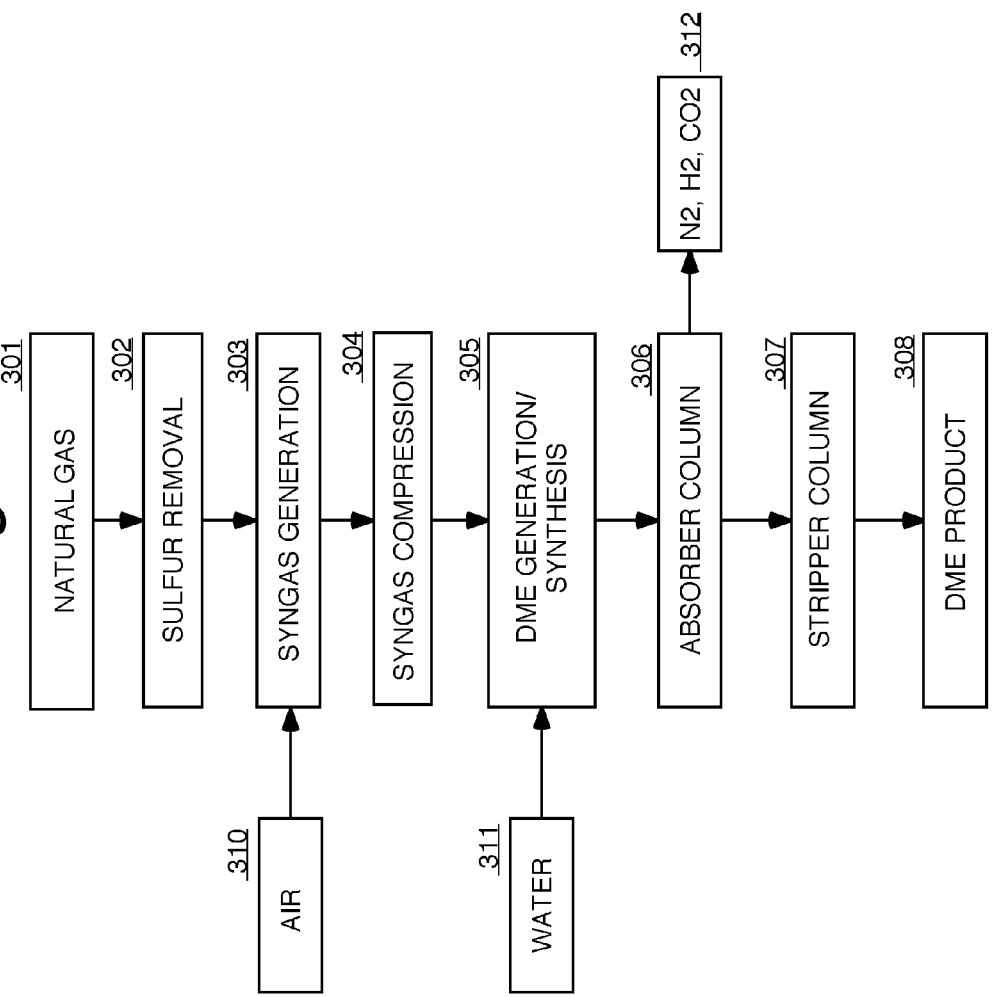

SYSTEMS AND METHODS FOR MANUFACTURE OF DIMETHYL ETHER (DME) FROM NATURAL GAS AND FLARE GAS FEEDSTOCK

REFERENCE TO RELATED APPLICATIONS

This application is a divisional of and claims the benefit of priority to application U.S. Ser. No. 14/953,268, now U.S. Pat. No. 9,643,906, filed on 27 Nov. 2015, and entitled "SYSTEMS AND METHODS FOR MANUFACTURE OF DIMETHYL ETHER (DME) FROM NATURAL GAS AND FLARE GAS FEEDSTOCK," which itself is a nonprovisional of and claims the benefit of priority to provisional application U.S. Ser. No. 62/085,391, filed on 28 Nov. 2014, and entitled "DIMETHYL ETHER (DME), A DIESEL-SUBSTITUTE LIQUID FUEL, FROM NATURAL GAS AND FLARE GAS FEEDSTOCK," all of which are hereby incorporated by reference in their entireties herein.

FIELD OF THE INVENTION

The present invention relates to enabling the utilization of raw natural gas, such as flare gas, stranded gas, associated gas, and so on, for dimethyl ether (DME) production. More specifically, this invention relates to a mobile system for producing DME from any natural gas feedstock, wet or dry.

BACKGROUND OF THE INVENTION

The statements in this section merely provide background information related to the present disclosure and may not constitute prior art.

The U.S. is currently flaring so much stranded natural gas that the gas flares are visible from outer space. The world annually flares about 5,000 billion cubic feet (BCF) of stranded gas. This is equivalent to the annual gas usage of France and Italy combined, and represents about 5% of the world's gas production. It is estimated that in North Dakota alone, where oil production from fracking had reached 1 million barrels per day in 2014, around 36% of North Dakota's associated gas was flared—about 120 BCF/yr. All this flare gas produces significant quantities of $CO_2$ emissions, estimated to be about 7 million tons of $CO_2$-equivalents into the atmosphere from North Dakota's flaring, or the emissions from about 1.3 million cars, while producing no useful product. Furthermore, North America is facing a vast abundance of natural gas generally, driving natural gas prices to historical lows, making it an ideal feedstock for liquid fuel production.

Flaring of natural gas entails significant loss of income for oil and gas producers that could be earned by selling the natural gas product. Still more financial losses are entailed by failing to make use of the energy content of the flared gas to generate power. As a result, such producers must buy their electric power from the grid, or even worse, generate it themselves at significant cost (typically USD$0.40/kWh) using on-site diesel generators consuming expensive diesel fuel. Furthermore, the large-scale flaring of natural gas has raised environmental issues that could cause state and/or federal regulators to act to fine, shutdown, or highly regulate their operations.

The United States oil and gas industry annually flared approximately 7.1 billion cubic meters (bcm), or 250 billion cubic feet (bcf) in 2011 (Source: Global Gas Flaring Reduction Partnership, *Estimated Flared Volumes from Satellite Data,* 2007-2011, 2013), and the situation has only gotten worse. "Flaring will escalate as oil producers approach the milestone of 1 million barrels a day from the Bakken formation, a 360-million-year-old shale bed two miles underground. About 10,100 wells produced 29 million barrels of oil in January 2014, according to the North Dakota Industrial Commission. Drillers flared 340 million cubic feet (mmcf), or 34 percent, of the 1 billion cubic feet of natural gas produced per day in January 2014, about twice as much as the 184 million cubic feet burned per day in 2011, said Marcus Stewart, an analyst at Denver-based Bentek Energy. 'The lost revenue adds up to $1.4 million each day,' said Stewart. Energy executives say economic realities force them to start producing oil from wells before infrastructure is in place to haul away less-valuable natural gas." (Source: Jennifer Oldham, *A Landscape of Fire Rises Over North Dakota's Gas Fields,* Bloomberg News, Apr. 7, 2014)

Canada also has a significant flaring problem. It is estimated that Canada flared 2.4 billion $m^3$ per year in 2011 (Source: Global Gas Flaring Reduction Partnership, *Estimated Flared Volumes from Satellite Data,* 2007-2011, 2013.) It is estimated that the Canadian province of Alberta alone flared 868 million $m^3$ and vented another 333 million $m^3$ in 2007. (Source: Bott, R. D., *Flaring Questions and Answers, 2nd ed.,* Canadian Centre for Energy Information, 2007.) A similar situation holds around the world, with significant quantities of gas being flared in Russia, Nigeria, and other parts of the world.

Flaring produces significant quantities of $CO_2$ emissions while producing no useful product. If this wasted flare gas could be utilized for powering drilling rigs and other oil field equipment, used to produce liquid fuel, and/or transported for sale to market, significant environmental and economic benefits would accrue.

Furthermore, gas produced as a by-product of fracking shale for oil is often rich in natural gas liquids (NGLs), including, but not limited to, in the Bakken formation of North Dakota, United States. Although natural gas prices are at a historic low in the United States, the high concentration of NGLs justifies gathering and processing the gas. However, as gas gathering infrastructure is put into place, and statutory restrictions kick in after 12 months after initial drilling, flaring on old wells may be reduced. Unfortunately, newly drilled wells as well as wells far from pipeline infrastructure will continue to be flared. This high variability and uncertainty in flaring quantities make it extremely difficult to plan and effectively size traditional gas gathering and pipeline infrastructure to minimize flaring.

It is highly financially and environmentally disadvantageous to flare valuable natural gas that could be sold for profit. It is even more financially and environmentally disadvantageous to utilize large quantities of diesel for power generation while at the same time flaring a feedstock that could be doing the same job. The problem is that liquids-rich raw natural gas cannot be used in generators and cannot be transported by truck.

Whereas the problem of flare gas was previously recognized, two known solutions included (1) pipelines to transport the raw natural gas to natural gas plants/refineries, and (2) mobile systems to process the flare gas on-site. These will be briefly discussed in turn. First, pipelines can be built to transport the raw natural gas from oil fields currently flaring to natural gas plants/refineries. This has several drawbacks, including complexity, cost, long-lead time, and permitting issues associated with building pipelines. An additional problem with pipelines is the flare volumes are highly uncertain and variable, making it difficult to plan pipeline construction. Additionally, pipelines cannot be deployed quickly to address the existing problem in real-time, nor can they be moved when flare volumes decrease. Finally, even if pipelines could be built, natural gas plants are highly expensive and large, capital-intensive infrastructure projects that would take time and large capital to finance and build.

Secondly, existing mobile systems have many shortcomings; all existing mobile systems are designed to either capture NGLs or produce dry generator gas. Some existing mobile systems are designed for extracting NGLs from the raw natural gas, and then flare the remaining methane and ethane because it is unusable in existing gensets. Other existing mobile systems generate high-quality (lean) methane for CNG production or pipelines, and flare the remaining NGLs because it has high ethane content (and hence a high vapor pressure), and cannot be transported in existing tanks. Many mobile systems utilize the Joule-Thompson (J-T) effect, and cannot remove a substantial portion of the ethane content in the flare gas, resulting in a gas mixture that is unpractical to use in existing, unmodified gensets. The system design presented in the present application solves the problems with both existing pipeline-based solutions as well as existing mobile systems by producing a transportable fuel from the raw natural gas feedstock.

Therefore, there exists an important need for a solution to address the problem of utilizing raw natural gas (wet or dry), which may have significant quantities of NGLs, to the maximum extent and to minimize or eliminate flaring, while still meeting the operators' requirements of a highly variable and uncertain flow rate in the raw natural gas stream.

Accordingly, as recognized by the present inventors, what are needed are a novel method, apparatus, and system for converting raw natural gas into a liquid stream that can be easily transported by truck, and that can be utilized for transportation and/or power generation, or for other purposes in existing equipment. As recognized by the present inventors, what is also needed is a liquid fuel synthesis system that is compact, portable, and modular, and which can be easily and quickly delivered to, as well as removed from, flare gas sites as flaring volumes change and as natural gas infrastructure matures.

Therefore, it would be an advancement in the state of the art to provide an apparatus, system, and method for producing a liquid fuel from a raw natural gas source at or near an oil or gas site that flares its associated gas. It would also be an advancement in the state of the art to provide a compact, portable, and modular liquid fuel production apparatus that can be used anywhere there is stranded, flared, or low-value natural gas.

It is against this background that various embodiments of the present invention were developed.

BRIEF SUMMARY OF THE INVENTION

The DImethyl Ether from Methane ("DIEM") system would allow dimethyl ether, a diesel substitute, to be produced from low-value natural gas, such as wasted flare gas, stranded gas, and the like, at a cost substantially lower than petroleum-based diesel. DME can be used at 100% substitution on an unmodified diesel engine, utilizing 60-100 psi propane-rated storage tanks. DME is a sulfur-free, particulate-free, ultra-clean diesel fuel, that can be put directly to use without further refinement. Using surplus natural gas and flare gas for liquid fuel production yields significant environmental and economic benefits. The process would enhance the economic and energy security of the world through: a) reductions of imports of energy from volatile regions of the world; b) reductions in energy-related emissions, including greenhouse gases; and c) improvement in the energy and economic efficiency of the oil and gas sector.

The inventors have developed a unique design for a mobile system that reforms raw natural gas, using air without steam, to directly produce dimethyl ether (DME), a diesel substitute. The system first reforms the air-natural gas mixture at pressures close to ambient pressure, preferably at ambient pressure, and then compresses the resulting CO-hydrogen-nitrogen gas mixture to high pressures in the 100-2,000 psi range, preferably at around 300 psi and feeds the gas mixture through a combined reactor with a mixed catalyst bed which reacts the gas mixture directly into DME. The nitrogen is returned to the atmosphere. DME is an excellent diesel fuel, and can be used to displace significantly costlier and dirtier petroleum-based diesel fuel, while solving a critical problem with flaring and stranded gas utilization.

Existing competing technologies for dealing with stranded natural gas include hauling the flare gas by truck as CNG or LNG. These solutions are inferior to the DIEM because of the logistical complexity and cost of transporting CNG and LNG compared to transporting a room-temperature liquid such as DME produced on site by the DIEM. Alternatively, DME today is currently produced in massive stationary industrial-scale chemical plants, which must be supplied with pipeline natural gas or coal, which are commercial feedstocks that can be expensive, as opposed to flare gas, which is free and a hindrance. Furthermore, making DME out of marketable fuels does nothing to reduce flaring or $CO_2$ emissions. Systems that make methanol out of flare gas have frequently been proposed, but such systems require steam and oxygen, making their product methanol expensive. Thus, the DIEM is uniquely advantageous. By using the DIEM, the roughly 120 billion cubic feet per year that was flared in North Dakota in 2014 could be converted into roughly 3 million tons of DME.

Accordingly, embodiments of the present invention include a mobile system for converting raw natural gas into dimethyl ether (DME) using air as a source of oxygen, comprising a syngas generator for generating syngas from the raw natural gas and air; a syngas compressor for compressing the syngas; a DME synthesis unit for synthesizing the DME from the compressed syngas, having a single reaction chamber comprising a mixed catalyst bed of hydrogenation and dehydration catalysts; and a DME purification unit for separating the DME from side products in the DME synthesis unit to produce a purified DME stream.

Other embodiments of the present invention include the system described above, further comprising a sulfur removal unit for removing sulfur from the raw natural gas stream.

Other embodiments of the present invention include the system described above, wherein the mixed catalyst bed comprises a syngas-to-methanol synthesis catalyst and a methanol-to-DME dehydration catalyst.

Other embodiments of the present invention include the system described above, wherein the syngas-to-methanol synthesis catalyst is Cu—ZnO.

Other embodiments of the present invention include the system described above, wherein the methanol-to-DME dehydration catalyst is gamma alumina.

Other embodiments of the present invention include the system described above, wherein the mixed catalyst bed comprises Cu—ZnO for methanol synthesis blended with gamma alumina for methanol dehydration to DME.

Other embodiments of the present invention include the system described above, wherein the DME purification unit further comprises an absorber column comprising an aqueous solvent system for absorbing the DME, while the effluent gases ($N_2$, $H_2$, CO, and $CO_2$) are exhausted.

Other embodiments of the present invention include the system described above, wherein the effluent gases are combusted to provide power to operate the syngas compressor.

Other embodiments of the present invention include the system described above, wherein the DME purification unit further comprises a stripper column, wherein rich DME solvent solution is sent to the stripper column, wherein the DME is distilled from the aqueous solvent, and a resulting lean solvent is recycled back to the absorber column.

Other embodiments of the present invention include the system described above, wherein the syngas generator comprises an air reforming unit for reforming the raw natural gas and air in the presence of a steam reforming catalyst.

Other embodiments of the present invention include the system described above, wherein air enriched in oxygen is added to the air reforming unit to increase concentrations of hydrogen and carbon monoxide in the syngas.

Other embodiments of the present invention include the system described above, wherein water is added to the air reforming unit to prevent catalyst coking.

Other embodiments of the present invention include the system described above, wherein water is recycled to the air reforming unit from a condenser downstream from an air recycling unit.

Other embodiments of the present invention include the system described above, wherein distilled water is converted to steam inside the air reforming unit.

Other embodiments of the present invention include the system described above, wherein a gas mixer mixes raw natural gas, air, and steam before these gases pass through a catalyst bed.

Other embodiments of the present invention include the system described above, wherein natural gas and air are preheated to improve carbon monoxide yield.

Other embodiments of the present invention include the system described above, wherein some of the syngas is recirculated back to the reformer to prevent hot spots in the catalyst.

Yet other embodiments of the present invention include a method for converting a raw natural gas into dimethyl ether (DME) using air as a source of oxygen, comprising generating syngas in an air reformer from a feedstock comprising the raw natural gas and the air, wherein the syngas comprises carbon monoxide, hydrogen, and nitrogen from the air; compressing the syngas that comprises the carbon monoxide, the hydrogen, and the nitrogen; synthesizing a DME mixture from the syngas in a single reaction chamber using a mixed catalyst bed; and purifying the DME mixture to produce a purified DME stream, wherein essentially all carbon in the purified DME stream comes from the raw natural gas, and wherein unreacted nitrogen from the DME mixture is returned to atmosphere.

Other embodiments of the present invention include the method described above, further comprising removing sulfur from the raw natural gas.

Other embodiments of the present invention include the method described above, wherein the mixed catalyst bed comprises a syngas-to-methanol synthesis catalyst and a methanol-to-DME dehydration catalyst.

Other embodiments of the present invention include the method described above, wherein the syngas-to-methanol synthesis catalyst is Cu—ZnO.

Other embodiments of the present invention include the method described above, wherein the methanol-to-DME dehydration catalyst is gamma alumina.

Other embodiments of the present invention include the method described above, wherein the mixed catalyst bed comprises Cu—ZnO for methanol synthesis blended with gamma alumina for methanol dehydration to DME.

Other embodiments of the present invention include the method described above, wherein the purifying of the DME utilizes an absorber column comprising an aqueous solvent for absorbing the DME, while effluent gases (N2, H2, CO, and CO2) are exhausted.

Other embodiments of the present invention include the method described above, wherein the effluent gases are combusted to provide power to the compressing step.

Other embodiments of the present invention include the method described above, wherein the purifying of the DME further utilizes a stripper column, wherein DME-rich solvent solution is sent to the stripper column, and wherein the DME is distilled from the aqueous solvent, and a resulting lean solvent is recycled back to the absorber column.

Other embodiments of the present invention include the method described above, wherein the generating the syngas comprises reforming the raw natural gas and the air in a presence of a steam reforming catalyst in the air reformer.

Other embodiments of the present invention include the method described above, wherein air enriched in oxygen is used to increase concentrations of hydrogen and carbon monoxide in the syngas.

Other embodiments of the present invention include the method described above, wherein up to 40% air enrichment is utilized, eliminating a need for a large oxygen production system.

Other embodiments of the present invention include the method described above, wherein water is added to the air reformer to prevent catalyst coking.

Other embodiments of the present invention include the method described above, wherein the water is recycled to the air reformer from a condenser downstream from an air recycling unit.

Other embodiments of the present invention include the method described above, wherein a water addition rate is controlled to minimize conversion of carbon monoxide to carbon dioxide.

Other embodiments of the present invention include the method described above, wherein distilled water is converted to steam inside the air reformer.

Other embodiments of the present invention include the method described above, wherein gases in the air reformer are well mixed before the air reformer's catalyst bed to improve the air reformer's performance, wherein a gas mixer mixes the raw natural gas and the air before these gases pass through the air reformer's catalyst bed.

Other embodiments of the present invention include the method described above, wherein some of the syngas is recirculated back to the air reformer to prevent hot spots in the mixed catalyst bed.

Other embodiments of the present invention include the method described above, wherein the natural gas and the air are preheated to improve carbon monoxide yield.

Other embodiments of the present invention include the method described above, wherein the air reformer operates at a high-temperature but low pressure, whereas the single reaction chamber operates at high pressure but low temperature. Other embodiments of the present invention include the method described above, wherein a temperature of the air reformer is above 700° C. (973 K) at atmospheric pressure (1 bar). Other embodiments of the present invention include the method described above, wherein a temperature of the single reaction chamber is below 400° C. (673 K) at a pressure between 100 and 2,000 psi (6-140 bar). That is, the part of the system that is high-temperature is at a low pressure that does not challenge steel, and the part of the system that is high-pressure is at a low temperature that similarly does not challenge steel. This allows for a compact and portable design for a system designed for field deployment in a mobile unit.

Other embodiments of the present invention include the method described above, wherein an in-reactor cooling system with a water coolant is used to reject heat and control DME reactor isotherms in the single reaction chamber.

Other embodiments of the present invention include the method described above, wherein the water coolant is converted to high temperature, high pressure steam and used in a reboiler to purify the DME mixture in a stripper column.

Other features, utilities, and advantages of the various embodiments of the invention will be apparent from the following more particular description of various embodiments of the present invention.

BRIEF DESCRIPTION OF THE DRAWINGS

The invention will be understood by the following detailed description in conjunction with the accompanying drawings, wherein like reference numerals designate like structural elements, in which:

FIGS. 2A and 2B show a schematic diagram of one embodiment of an air reforming unit and DME synthesis system according to one embodiment of the present invention.

FIG. 3 shows a flowchart of a process for producing DME from raw natural gas according to one embodiment of the present invention.

DETAILED DESCRIPTION OF THE INVENTION

Figure 1:
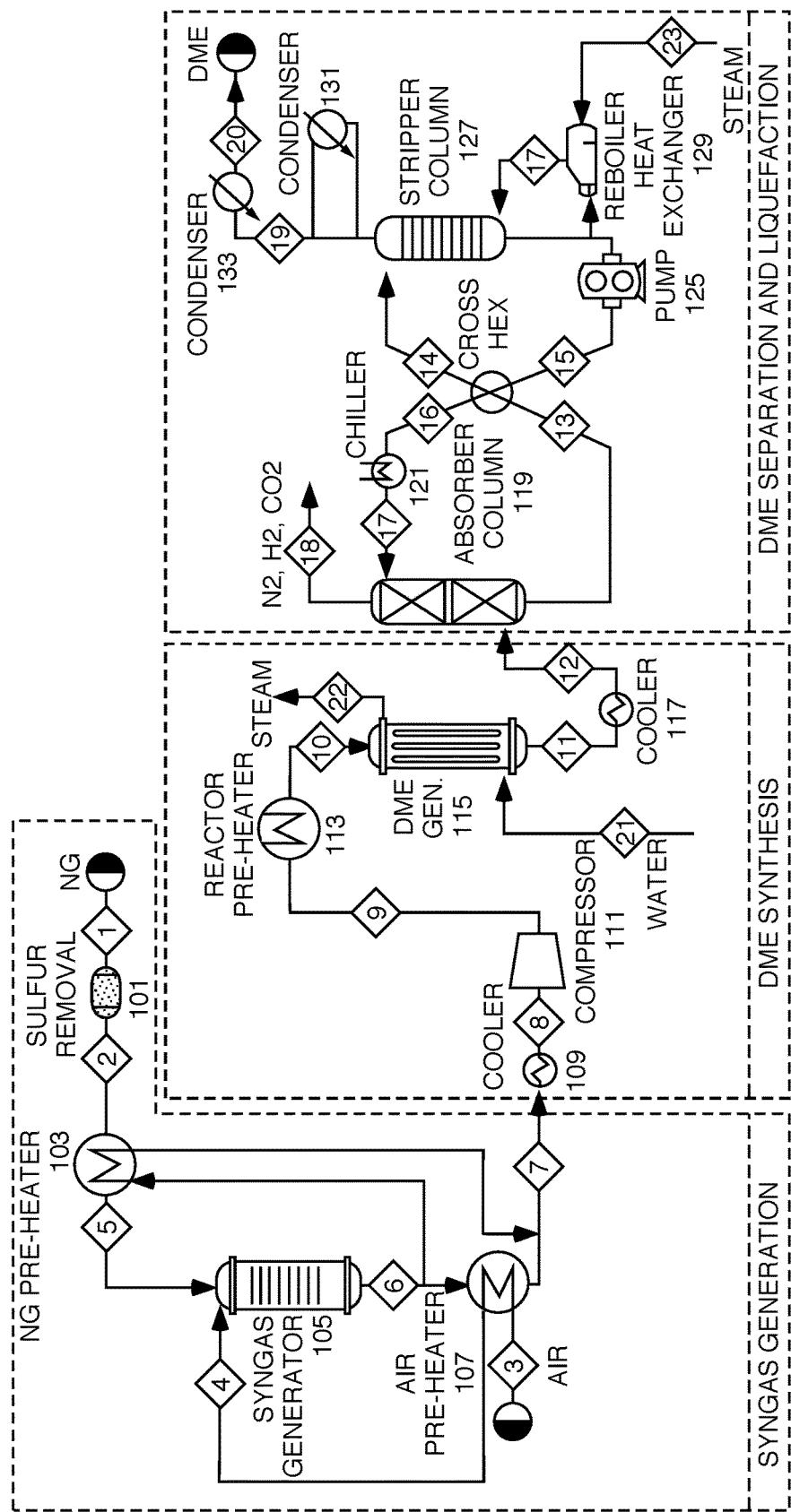
FIG. 1 shows a block diagram of one embodiment of a DImethyl Ether from Methane (DIEM) system according to one embodiment of the present invention.

The following description is merely exemplary in nature and is in no way intended to limit the scope of the present disclosure, application, or uses.

Definitions

The following terms are provided for illustrative and explanatory purposes only, and are not intended to limit the application, intended uses, or scope of the present invention.

Throughout this disclosure "DIEM-170," "full scale" apparatus, or any reference to a single full-scale module, will refer to an apparatus module that can process about 170 mcf (thousand cubic feet) of raw natural gas per day. Multiple modules can be combined for higher gas flow rates. These product flow estimates are provided for explanation purposes only, and are not intended to be limiting the scope of the present invention in any way. DIEM is a shorthand for "DImethyl Ether from Methane" system.

The symbols cf, CF, scf, and SCF shall all stand for standard cubic feet ($ft^3$). The symbols mcf, MCF, and kcf will all stand for a thousand standard cubic feet (1,000 scf). The symbols MMCF, MMcf, and mmcf will all stand for a million standard cubic feet (1,000,000 scf or 1,000 mcf). The word "day" shall mean "a day of operations," which shall be a 24-hour day, but could also be an 8-hour day, a 12-hour day, or some other amount of operational time. 1 scf=0.02832 standard $m^3$=28.32 L.

Natural gas at the wellhead is commonly a mixture of methane (C1) with other hydrocarbons, including ethane (C2), propane (C3), butane (C4), pentane (C5), and hexane and higher (C6+). Wellhead natural gas also contains other compounds such as water vapor ($H_2O$), hydrogen sulfide ($H_2S$), carbon dioxide ($CO_2$), oxygen ($O_2$), and nitrogen ($N_2$). Also known as raw natural gas. Pure methane is also included within this definition.

Associated gas is natural gas produced as a by-product of oil drilling, either conventional or unconventional extraction (such as hydraulic fracking for tight oil). Also known as raw natural gas.

Flare gas is natural gas, usually associated gas, that is flared (burned for no useful purpose) because natural gas pipelines are not in place when the oil well is drilled. Also known as raw natural gas.

Stranded gas is natural gas, usually associated gas that is flared, that cannot be brought to market either because it is off-shore or too far from natural gas pipelines/infrastructure. Also known as raw natural gas.

As used herein, the phrase raw natural gas, or even more simply natural gas, shall be interchangeable with, and could mean, all of the following: unprocessed natural gas, associated gas, flare gas, and/or stranded gas, and is meant to encompass all such raw natural gas sources.

Wet gas is natural gas that contains a high proportion of C2+ components (typically more than 10%). Wet gas is frequently also saturated with water vapor. This is an approximate definition often used by those skilled in the art.

Dry gas is natural gas with typically less than 5% C3+ components, or typically less than 10% C2+ components. This is an approximate definition often used by those skilled in the art.

Natural gas liquids (NGLs) are C3+ components, including propane and heavier hydrocarbons, and may include small amounts of methane and ethane. Other definitions sometimes include ethane as an NGL (natural gas liquid).

Y-grade is an informal standard used to specify NGL requirements. One common definition for Y-grade is a hydrocarbon mixture having essentially no methane and a low ethane content, typically having a vapor pressure of no more than 17.2 bar/250 psia at 38° C./100° F. Y-grade is not necessarily limited to 17.2 bar/250 psi, but refers to a hydrocarbon mixture that has essentially no methane and a low fraction of ethane, and accordingly a vapor pressure that is lower than raw wellhead gas.

LPG is an acronym for Liquefied Petroleum Gas, which is generally a term for pressurized, processed gas mixtures of C3+ components, most commonly primarily propane and butane.

CNG is an acronym for Compressed Natural Gas, which is typically mostly methane (C1) compressed to a pressure above approximately 140 bar/2,000 psig, although higher or lower pressures are also possible.

LNG is an acronym for Liquefied Natural Gas, which is typically mostly methane (C1) at a pressure and a temperature in which it is a liquid phase.

A column is used to separate a fluid mixture into its constituent parts based on differences in the volatility of components in a boiling liquid mixture. Distillation is a physical separation process and not a chemical reaction.

DME stands for dimethyl ether, the simplest ether, and an excellent diesel engine fuel.

Overview of the Diem System

It is highly disadvantageous—both from a financial and an environmental perspective—to flare natural gas that could be sold for a profit. It is even more disadvantageous to spend large amounts of money on diesel fuel for power generation, and at the same time flare methane that could be doing the same job. The problem is that raw natural gas cannot be used in generators and cannot be transported by truck. The inventors recognized that what is needed is a mobile system that can go to a well-site that is currently flaring gas, and process the raw natural gas into a liquid fuel—DME—that can be used for transportation, to generate power, or for other purposes, and/or that can be transported for sale. It is to meet this unmet need that the inventors have developed the DImethyl Ether from Methane (DIEM) system.

The DIEM is a truck-mobile methane-to-DME conversion system scaled to meet local needs. The DIEM system can use any kind of natural gas, wet or dry, as its feedstock, to produce dimethyl ether, which is a viable and clean diesel fuel without refining. In what follows, it is assumed that the feedstock is pure methane. The presence of higher hydrocarbons in the gas increases the yield in proportion that the total amount of carbon in the gas is increased. The system works using a mixed heterogeneous catalyst bed—no expensive precious metal catalysts are needed. First, the methane is reformed at pressures close to ambient (0.5-10 bar), preferably at ambient pressure, using preheated air over Ni catalyst to produce hydrogen and carbon monoxide. The resulting gas is then compressed to high pressures (5-100 bar), preferably 20 bar and then reacted in a mixed Cu—ZnO and gamma alumina catalyst bed to produce methanol, which dehydrates in place immediately to form dimethyl ether. This allows dimethyl ether production in a one-pass reactor, with excellent performance despite the presence of nitrogen, eliminating the need for expensive oxygen or a boiler. The system is simple enough overall to enable implementation in a compact field-mobile form. From 170 mcf/day of flare gas, the system can produce about 3 tons/day of DME. In short, the new DIEM system can use waste flare gas or stranded natural gas, located anywhere in the world, and produce a valuable diesel engine fuel.

Process Overview and Chemistry: Dimethyl ether (DME) is produced from the low-pressure catalytic partial air oxidation of natural gas to syngas (CO and $H_2$) at low pressures (0.5-10 bar), preferably at ambient pressure. The syngas is then compressed to high pressures (5-100 bar), preferably 20 bar, and fed into a single-step dimethyl ether synthesis reactor using mixed methanol synthesis and methanol dehydration catalysts to produce dimethyl ether. The DME is purified from background constituents using an absorber/stripper column, and the product liquefied. The principal reactions for the DIEM are given in reactions (1)-(6):

Syngas Generation from Natural Gas with Air $$N_2+CH_4+\tfrac{1}{2}O_2 \leftrightharpoons 2H_2+CO+N_2,\ \Delta H_{298}=-35.9\ \text{kJ/mol},\ \Delta G_{298}=-86.7\ \text{kJ/mol} \quad (1)$$

DME Synthesis from Syngas $$CO+2H_2 \leftrightharpoons CH_3OH,\ \Delta H_{298}=-90.5\ \text{kJ/mol},\ \Delta G_{298}=-25.1\ \text{kJ/mol} \quad (2)$$

$$2\ CH_3OH \leftrightharpoons CH_3OCH_3+H_2O,\ \Delta H_{298}=-23.9\ \text{kJ/mol},\ \Delta G_{298}=-16.6\ \text{kJ/mol} \quad (3)$$

$$CO+H_2O \leftrightharpoons CO_2+H_2,\ \Delta H_{298}=-41.2\ \text{kJ/mol},\ \Delta G_{298}=-28.6\ \text{kJ/mol} \quad (4)$$

Overall DME Synthesis from Syngas $$3\ CO+3H_2 \leftrightharpoons CH_3OCH_3CO_2,\ \Delta H_{298}=-246.1\ \text{kJ/mol},\ \Delta G_{298}=-95.4\ \text{kJ/mol} \quad (5)$$

Net Reaction (Natural Gas to DME)

$$3CH_4+3/2O_2 \leftrightharpoons CH_3OCH_3+3\ H_2+CO_2,\ \Delta H_{298}=-282\ \text{kJ/mol},\ \Delta G_{298}=-182.1\ \text{kJ/mol} \quad (6)$$

Process Flow Diagram: One embodiment of a process flow diagram and stream summary for the DIEM process is shown in FIG. 1 and Table 1, in which 3,000 kg/day of 98% purity dimethyl ether product is generated from a starting flow rate of 10,000 SLPM air and 3,300 SLPM of methane.

In one embodiment, the DIEM contains three main process sub-systems: (1) Syngas Generation, (2) DME Synthesis, and (3) DME Separation and Liquefaction, which are highlighted in FIG. 1 and discussed in turn below. Flow rates of inputs and products for this embodiment of the DIEM are shown in Table 1.

TABLE 1

| DIEM System Flow Rates | |
|---|---|
| Methane feed rate | 3,300 L/min = 2.4 kg/min = 170 mcf/day |
| Air feed rate | 10,000 L/min |
| DME Production Rate | 125 kg/hour = 3,000 kg/day = 1,180 gal/day (@ 25° C.) |
| Hydrogen production rate | 3,300 L/min |
| Thermal power available from $H_2$ | 720 kWt |
| Power requirement | 180 kWe |
| Value of DME product | ~$3,000/day |

Figure 2A:
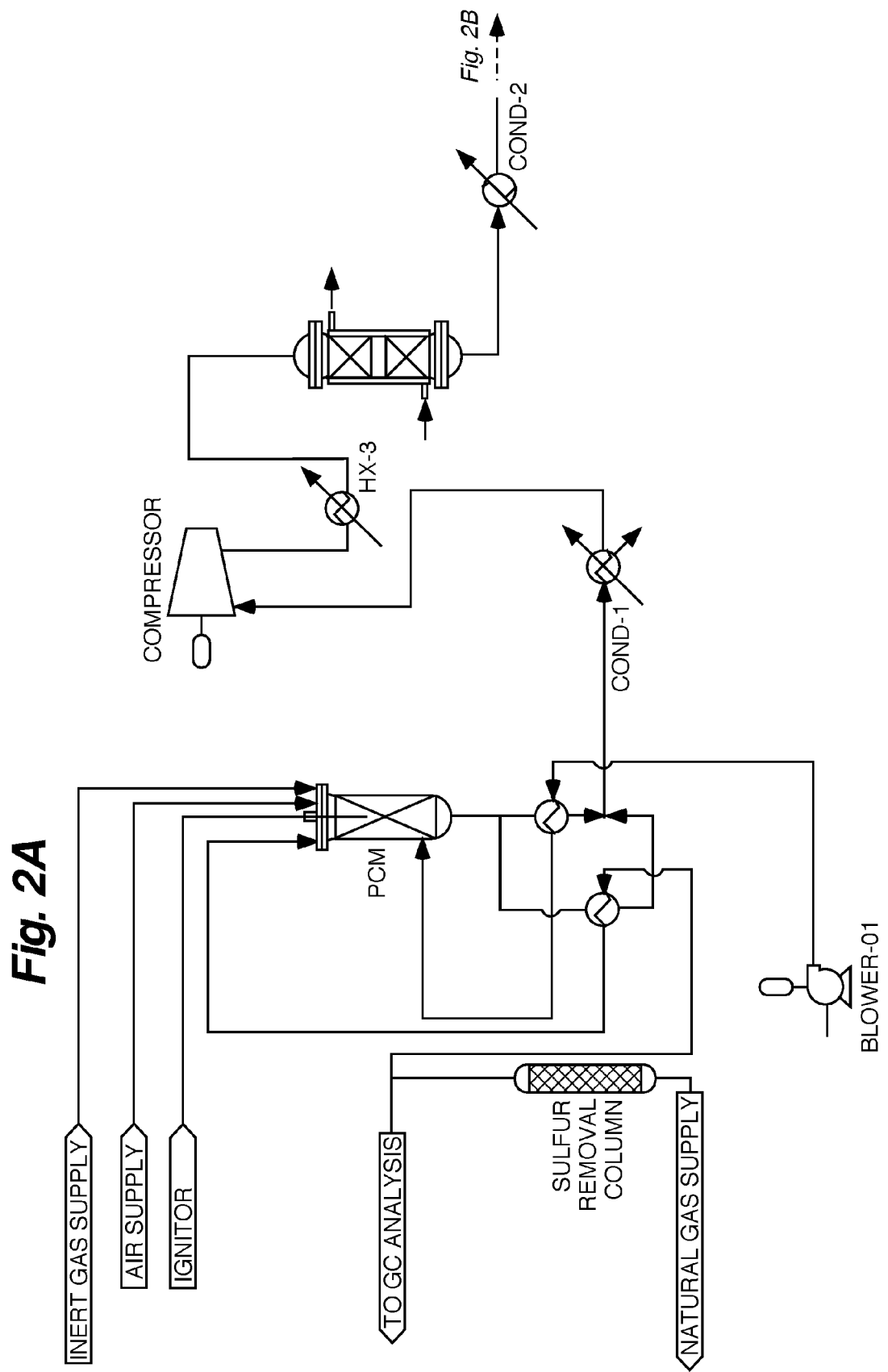

Syngas Generation: As shown in FIG. 1, to prevent downstream catalyst poisoning, the natural gas (Stream 1) is preconditioned with a desulfurization catalyst to reduce background sulfur concentration below 1 ppmv. The reactant gases methane (Stream 2) and air (Stream 3) are then preheated to temperatures between 300 K and 1100 K, preferably to 600 K before entering the Syngas Generator (Streams 4 and 5). This is accomplished by using gas heat exchangers and the excess heat from the syngas exiting the Syngas Generator (Stream 6). The Syngas Generator is operated preferably at 1 bar and 1080 K, and at these conditions a stream with a $H_2/CO$ mole ratio of approximately 2:1 (34.3% $H_2$, 17.2% CO) is generated from the reactor. FIGS. 2A and 2B shows a schematic of one embodiment of an air reforming unit useable in some embodiments of the present invention.

DME Generation: Product gas from Syngas Generator (Stream 7) is cooled to temperature at which significant fraction of water vapor condenses, preferably to 308 K and the condensed water is removed from the syngas. Dry syngas is compressed to high pressures in the range 5-100 bar, preferably to 20 bar with a compressor in Stream 9, and then heated to temperatures in the 460 K-540 K range, preferably to 500 K in Stream 10, prior to being sent to the DME Generator. The DME Generator operates at temperatures in 490 K-570 K range, preferably at 500 K, and at high pressures 5-100 bar, preferably at 20 bar, and produces a gas stream containing DME (Streams 11-12). The DME synthesis reaction is significantly exothermic such that any temperature exotherm must be kept below 400° C. (673 K) to prevent formation of undesirable products, such as methane, and to avoid catalyst deactivation. In one embodiment, an in-reactor cooling system based on a shell and tube design with water coolant is used to reject the heat and control the DME reactor isotherms. The water coolant is then converted to high temperature, high pressure steam and used in the reboiler in Stream 17 to purify the DME in a stripper column. In the embodiment of DIEM described in Table 1, a total of 69 kW power is released by synthesis reaction (5), which is significantly higher than the reboiler duty requirement of 20 kW.

Multiple reactors of can be used for synthesis of DME. Many reactor designs can be used to reject the heat generated by synthesis of DME. The heat can be removed inside the synthesis reactor (non-adiabatic reactor) as well as outside of the synthesis reactor (adiabatic reactor).

For non-adiabatic reactors, designs other than shell and tube can be used for rejecting the heat of the synthesis reaction. In one embodiment, coiled or otherwise shaped tubes in which cooling liquid is circulated can be placed in the catalyst bed to cool the catalyst. In another embodiment, the heat of reaction can be used to preheat the syngas using an open tube heat exchanger design, thus combining syngas preheating and catalyst cooling in a single step.

Reactors of different designs can be combined within the same system to achieve efficient synthesis of DME.

In addition to water, other substances for carrying heat can be used. For example, suitable heat transfer oils can be used, such as silicone oil.

DME Separation and Liquefaction: In one embodiment, gas from the DME Generator, Stream 11, is cooled to temperatures in the −10° C. to +20° C. range, preferably to 0° C., before being sent to the absorber column in Stream 12. DME is absorbed into an aqueous solvent system while the effluent gases ($N_2$, $H_2$, CO, and $CO_2$) are exhausted in the absorber column overhead in Stream 18. In one embodiment, these gases are combusted to give about 240 $kW_t$, which is sufficient to generate about 80 $kW_e$ of auxiliary electrical power to operate the syngas compressor for this embodiment. The DME-rich solvent solution (Streams 13-14) is sent to the stripper column, where DME is distilled from the aqueous solvent, and the resulting lean solvent (Streams 15-17) is recycled back to the absorber column.

The DME product is then condensed and collected from the overhead of the stripper column (Stream 20) to generate a purified DME stream.

Figure 4:
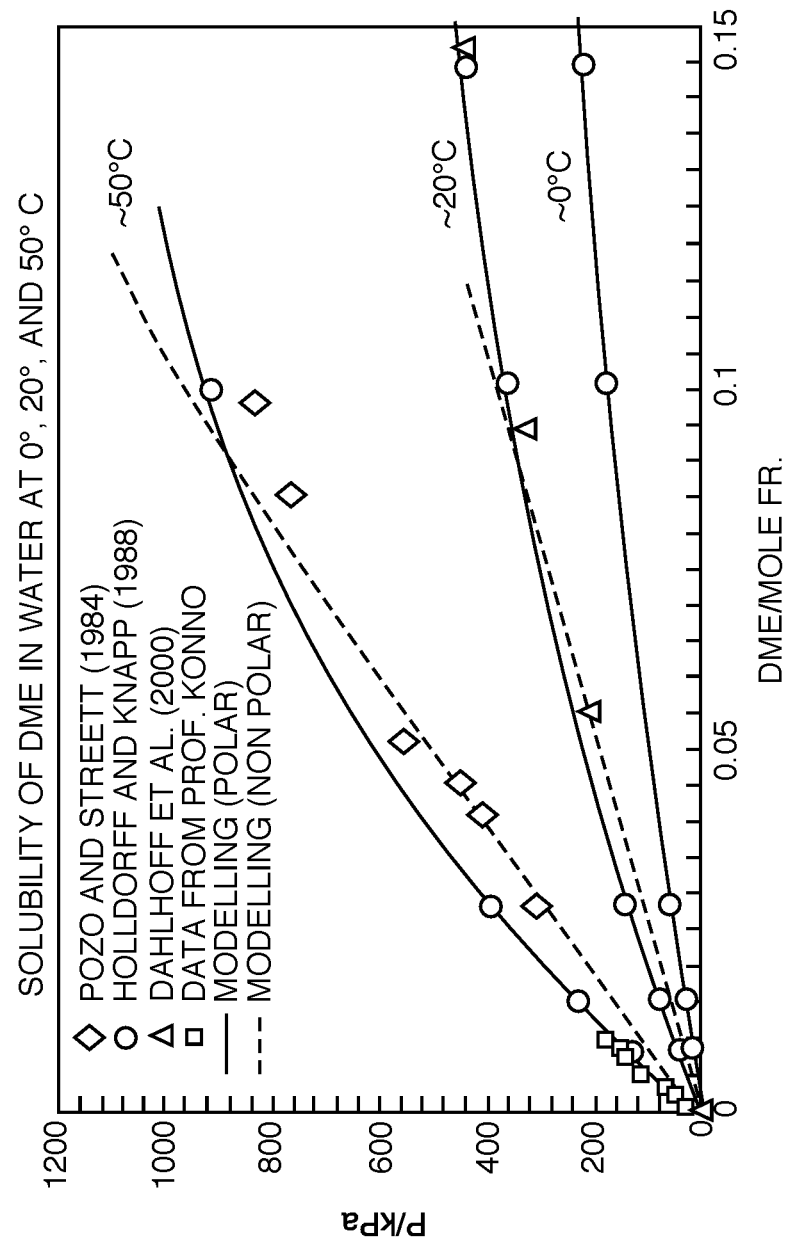
FIG. 4 shows DME-water Vapor-Liquid Equilibria (VLE) data for several temperatures, useful when designing the DIEM.

In embodiments described below, the DME Separation and Liquefaction process was designed analytically using VLE data for DME and water mixtures, and material and energy balance calculations. All key parameters of the separation process, including the lean and rich loading, recirculation rate, reboiler and condenser duties, and heat exchangers duties were estimated from the VLE curves and from material and energy balances. Some of the DME-water Vapor-Liquid Equilibria (VLE) data for several temperatures are shown in FIG. 4. The data in FIG. 4 are from Chapoy, A., et al., 2011, *Potential DME Storage in Underground Caverns: Investigation of the Phase Behavior of the DME-Water System at Low Temperature*, Proceedings of the 7th International Conference on Gas Hydrates (ICGH 2011), Edinburgh, Scotland, United Kingdom, Jul. 17-21, 2011; Holldorff, H., and Knapp, H., 1988, *Binary vapor-liquid-liquid equilibrium of dimethyl ether—water and mutual solubilities of methyl chloride and water: experimental results and data reductions*, Fluid Phase Equilibr. 44, 195-209; and Pozo, M., and Streett, W. B., 1984, *Fluid phase equilibria for the system dimethyl ether/water from 50 to 220° C. and pressures to 50.9 MPa*, J. Chem. Eng. Data 29, 324-329, which are all hereby incorporated by reference in their entireties herein.

One of the embodiments of the DME separation process uses a pure water solvent at 0° C. and 20 bar.

Another embodiment of the DME separation process uses 30% (mole/mole) methanol in water solvent at 20° C. and 20 bar.

Various mixtures of methanol and water can be used for the DME separation process ranging from pure water to pure methanol.

In one embodiment, using a partial pressure of 1.3 bar, DME at the synthesis reactor exit, and choosing 0° C. as the operating temperature of the scrubber, one can obtain a rich loading of 10% mole fraction for the solvent leaving the scrubber. The lean loading is ~1%, which is set by the desired capture rate of 90% and the scrubber temperature. In one embodiment, the molar flow of DME entering the scrubber is 2.3 mol/s. Using material balance and solvent rich and lean loading, the recirculation rate is about 0.23 $m^3/h$ (~1 gpm).

Since the heat capacity of solvent with DME is less than that of the water, the upper limit of duties on the cooling and cross heat exchangers can be calculated assuming a temperature approach of 10° C. in the cross-heat exchanger. The pressure in the stripper was chosen to be approximately 5 bar, so that the DME vapor coming from the stripper can be liquefied without further compression. For the loading of 10% and 5 bar DME partial vapor pressure, the temperature of the stripper is approximately 120° C. from the published VLE data.

In one embodiment which uses 30% (mole/mole) methanol in water solvent, the effect of methanol byproduct coming from the DME reactor was studied by using the NRTL model. The NRTL parameters were obtained from Holdorff and Knaap (1988) and other sources. Addition of the 30% mole fraction methanol to the solvent increases the solubility of DME in solvent, and the separation can be done with the scrubber temperature of 20° C., with the same recirculation rates and heat exchanger duties.

Separation of DME can be achieved in many ways. The preferred embodiment uses a absorber/stripper column design with a water or a water/methanol solvent. Other embodiments may include cryogenic separation, gas separation membranes, solid absorbents, among other ways of separating the DME.

In one embodiment, DME can be separated by cooling the effluent of the DME synthesis reactor to temperature at which a majority of the DME condenses.

In another embodiment, a gas separation membrane can be used for DME separation. A suitable gas separation membrane can be used to directly separate DME from the other gases.

In another embodiment, a gas separation membrane can be used in the DME separation process. A suitable gas separation membrane can selectively remove one of the gas components of syngas, for example, hydrogen. After removal of hydrogen from syngas, DME concentration in the gas increases, which makes it easier to separate DME using other methods, such as cryogenic or absorption/desorption using a liquid solvent.

In another embodiment, a solid sorbent used in the DME separation process. A suitable solid sorbent can selectively remove DME from the syngas.

In another embodiment, a solid sorbent can be used in the DME separation process. A suitable solid sorbent can selectively remove one or more of the gas components from syngas. After removal of these components from syngas, DME concentration in the gas increases, which makes it easier to separate DME using other methods, such as cryogenic or absorption/desorption using a liquid solvent.

In one embodiment, the air used in the reformation is enriched to 25% oxygen. In another embodiment, the air used in the reformation is enriched to 30% oxygen. In another embodiment, the air used in the reformation is enriched to 35% oxygen. In another embodiment, the air used in the reformation is enriched to 40% oxygen. In one embodiment, the concentration of oxygen is adjusted as the process is operating to control the temperature of the reactor and ratios of CO, $H_2$ and $CO_2$ in the product.

In another embodiment, the air used in the reformation is enriched to between 21 and 95% oxygen.

In one embodiment, the nitrogen is used to control the heat produced during the process.

In one embodiment, the system requires no boiler to deliver steam to produce the product.

In one embodiment, there is provided a system to make DME using oxygen in air as a reactant feed. In one embodiment, there is provided a system to make DME requiring no outside source of water. In one embodiment, there is provided a system to make DME where net water requirement is very low to no water required.

Illustrative Schematics

FIG. 1 shows a schematic diagram of one embodiment of the DIEM according to the principles of present invention. This schematic diagram is illustrative of but one embodiment of the present invention and is not to be read as limiting the scope of the present invention, its uses, or its implementation. Syngas generation, DME synthesis, and DME separation/liquefaction unit processes are separated by dashed lines. Raw natural gas (NG) is first desulfurized at sulfur removal 101, and the desulfurized gas is preheated at preheater 103. Syngas is generated in syngas generator 105, where air used in the syngas generator is pre-heated at preheater 107. The syngas is cooled at cooler 109, then compressed at compressor 111, and pre-heated at reactor pre-heater 113. DME is generated at the DME generator 115 from syngas and water. The DME product is cooled in cooler 117. Finally, an absorber column 119, chiller 121, pump 125, stripper column 127, reboiler heat exchanger 129, and condensers 131 and 133 are used to separate and liquefy the DME product.

FIGS. 2A and 2B shows a schematic of one embodiment of an air reforming unit and DME synthesis system useable in some embodiments of the present invention.

FIG. 3 shows a flowchart of a process for producing DME from raw natural gas according to one embodiment of the present invention. An embodiment of the present invention is a method for converting natural gas 301 into DME product 308 as shown. First, any sulfur is removed from the raw natural gas stream as it may poison catalysts, as shown in step 302. Then syngas is generated from the desulfurized natural gas and air 310, as shown in step 303. The syngas is compressed utilizing a compressor, as shown in step 304. The compressed syngas and water 311 is converted into DME in the DME generation/synthesis step, as shown in step 305. An absorber column is used to remove $N_2$, $H_2$, $CO_2$, and so on 312, as shown in step 306. Finally, a stripper column 307 is utilized to separate and liquefy the final DME product 308.

Pilot Unit Description

The inventors have built and tested several embodiments of the present invention. These sections present various experimental results from such tests.

A DIEM pilot unit was built to demonstrate DIEM on a substantial scale. The unit was run with the methane feed rate up to 500 SLM, or 18 SCFM. CO yields in excess of 84% from the air reforming unit were demonstrated. With 70% yield of DME from syngas, the pilot unit would produce approximately 510 kg of DME per day.

Air enters the reformer unit from the top through a 3-inch air supply pipe. The air supply pipe is concentric with the flange on a top of the reformer. A plenum is constructed by welding a pipe cap to the flange in a concentric arrangement. Natural gas enters the plenum and then injected into the air supply pipe using injectors. Injectors direct velocity of the natural gas flow to provide two velocity components. One velocity component of the natural gas stream is collinear and opposite to the velocity of the air stream. The other velocity component is perpendicular to the velocity of the air stream and generates a swirl to improve mixing.

The water stream enters a plenum where water is vaporized on contact with hot metal. The resulting steam is injected alongside with the natural gas.

An igniter is used to ignite a gas mixture to preheat the reformer.

A layer of the ceramic foam is placed on top of the catalyst to protect catalyst from a thermal shock during reformer preheating. A perforated plate is placed on top of the catalyst bed to separate ceramic foam layer from the catalyst pellets.

The syngas stream from the reformer contains a significant amount of water vapor. This water vapor comes from the water added to the reforming process as well as from the reactions between methane and air. Before compressing the reformer gas in a compressor, the majority of the water vapor is removed in a condenser. The pilot unit condenser is of a single pass tube side and single pass shell side construction. Cooling water is on a shell side and the syngas is on a tube side. The tube bundle was constructed from approximately 250 tubes of 0.375-inch diameter, each tube being 5 feet long.

The compressor used is a four-stage compressor with inter-stage cooling. The compressor can compress a flow of 6000 Standard Liters per Minute (SLM) of reformer gas to a pressure of 600 psia, or approximately 40 bar. The compressor is driven by two electrical motor with a total power rating of 80 HP (107 kW). The compressor is capable of handling of 5× turndown.

After the compressor, the syngas is directed into the synthesis reactor detailed on FIG. 1. Before entering the reactor, the syngas (stream 9) is preheated in a gas preheater to a temperature above 200° C. The preheated syngas, stream 10, enters the synthesis reactor. In the pilot unit, the shell of the synthesis reactor is constructed from a 6-inch diameter heavy wall pipe, which is approximately 5 feet long. The top end of the reactor was flanged using a raised face gasketed flange rated at 800 pounds and the bottom end of the reactor is capped using a pipe cap with the same 800-pound rating. To preheat the catalyst and to remove the energy from the reactor, the internal tube coils and external cooling jacket were integrated into the reactor. The external cooling jacket was constructed from an 8-inch diameter pipe and a couple of rings. The heat transfer fluid is circulated in an annular space between the 6-inch pipe and 8-inch pipe. The temperature and the flow rate of the heat transfer fluid are controlled by a separate subsystem. This subsystem contains a recirculation pump with a variable frequency drive, a system for measuring a flow rate of heat transfer fluid, a reservoir tank with inert gas purge, an expansion tank and the cooling/heating elements.

Figure 5:
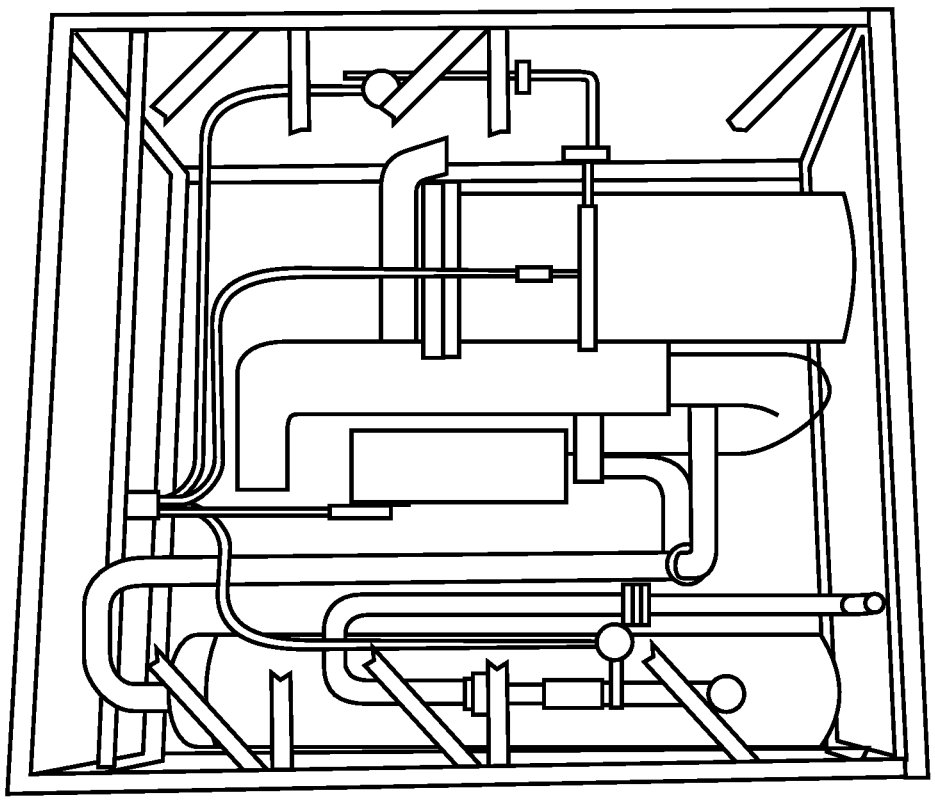
FIG. 5 illustrates a perspective view of a portion of a DIEM pilot unit (syngas generator subsystem), according to one embodiment of the present invention.

FIG. 5 illustrates a perspective view of a portion of the DIEM pilot unit (syngas generator subsystem), according to one embodiment of the present invention.

Figure 6:
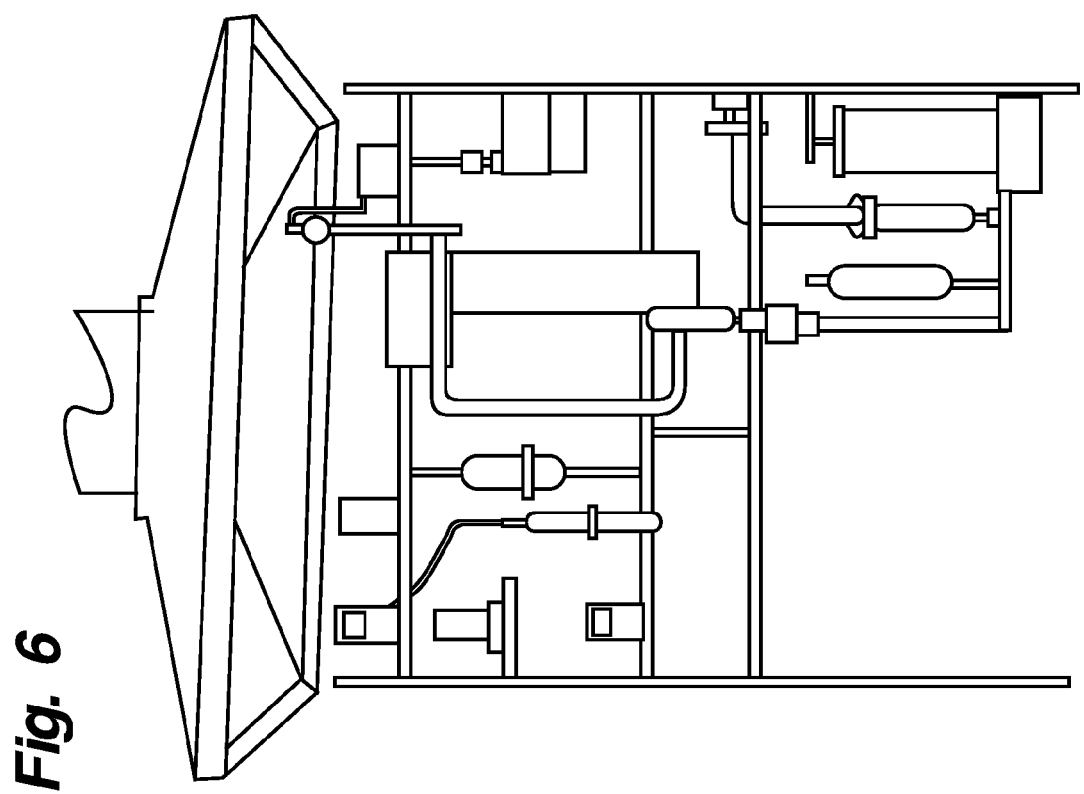
FIG. 6 illustrates a perspective view of another portion of the DIEM pilot unit (dimethyl ether synthesis reactor subsystem), according to one embodiment of the present invention.

FIG. 6 illustrates a perspective view of another portion of the DIEM pilot unit (dimethyl ether synthesis reactor subsystem), according to one embodiment of the present invention.

Figure 7:
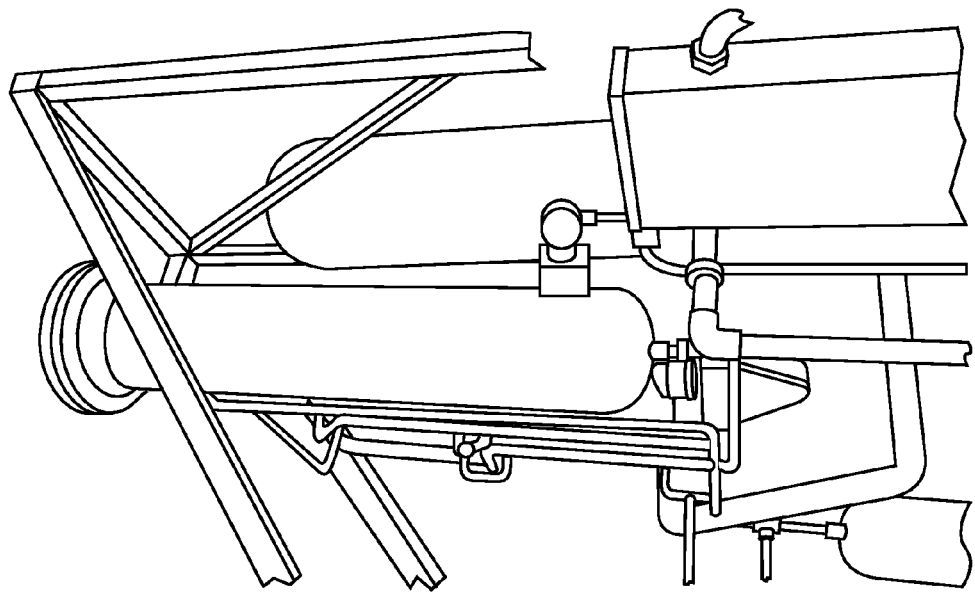
FIG. 7 illustrates a perspective view of another portion of the DIEM pilot unit (dimethyl ether separator and liquefaction subsystem), according to one embodiment of the present invention.

FIG. 7 illustrates a perspective view of another portion of the DIEM pilot unit (dimethyl ether separator and liquefaction subsystem), according to one embodiment of the present invention.

Performance of Pilot Unit Reformer with Air

To evaluate performance of the reformer, some meaningful quantitative metrics are needed. Carbon monoxide yield from methane is one such metric, and 100% conversion of methane to carbon monoxide would represent ideal operation of the reformer. However, 100% conversion of methane to carbon monoxide is not feasible, since some of the methane will be combusted to raise the temperature of the incoming gases and hence will not be available to make carbon monoxide product via the reforming process. In addition, thermodynamic equilibrium may limit carbon monoxide yield from methane. To investigate this, a computer simulation was performed to establish the maximum possible carbon monoxide yield in the reformer. This yield can be compared to the experimentally measured yield to establish how well the reformer works. For comparison with the experiment, let's consider the following case when the incoming gases (air and methane) are preheated to 400° C., the exit temperature of the reformer is 750° C., the molar ratio of water flow rate to methane flow rate is 1:4, and the air to methane ratio is 3.0. With the assumption that the reaction in the reformer reaches equilibrium, the calculated carbon monoxide yield is 83%, with the following calculated composition of dry gases out of the reformer: Hydrogen: 35.8%, Carbon monoxide: 15.4%, Carbon dioxide: 2.9%, Methane: 0.2%, Nitrogen, argon: balance.

These calculated numbers can be directly compared with the experimental results. In one test, the air and methane were preheated to the temperatures close to 400° C., the molar ratio of water flow rate to methane flow rate was approximately 1:4, and the temperature of gas exiting the reformer was approximately 750° C., the same conditions for which simulation was done. A CO yield of 84% was measured and the following composition of dry gases out of the reformer was measured: Hydrogen: 32.7%, Carbon monoxide: 16.2%, Carbon dioxide: 1.8%, Methane: 1.24%, Nitrogen, argon: balance.

Figure 8:
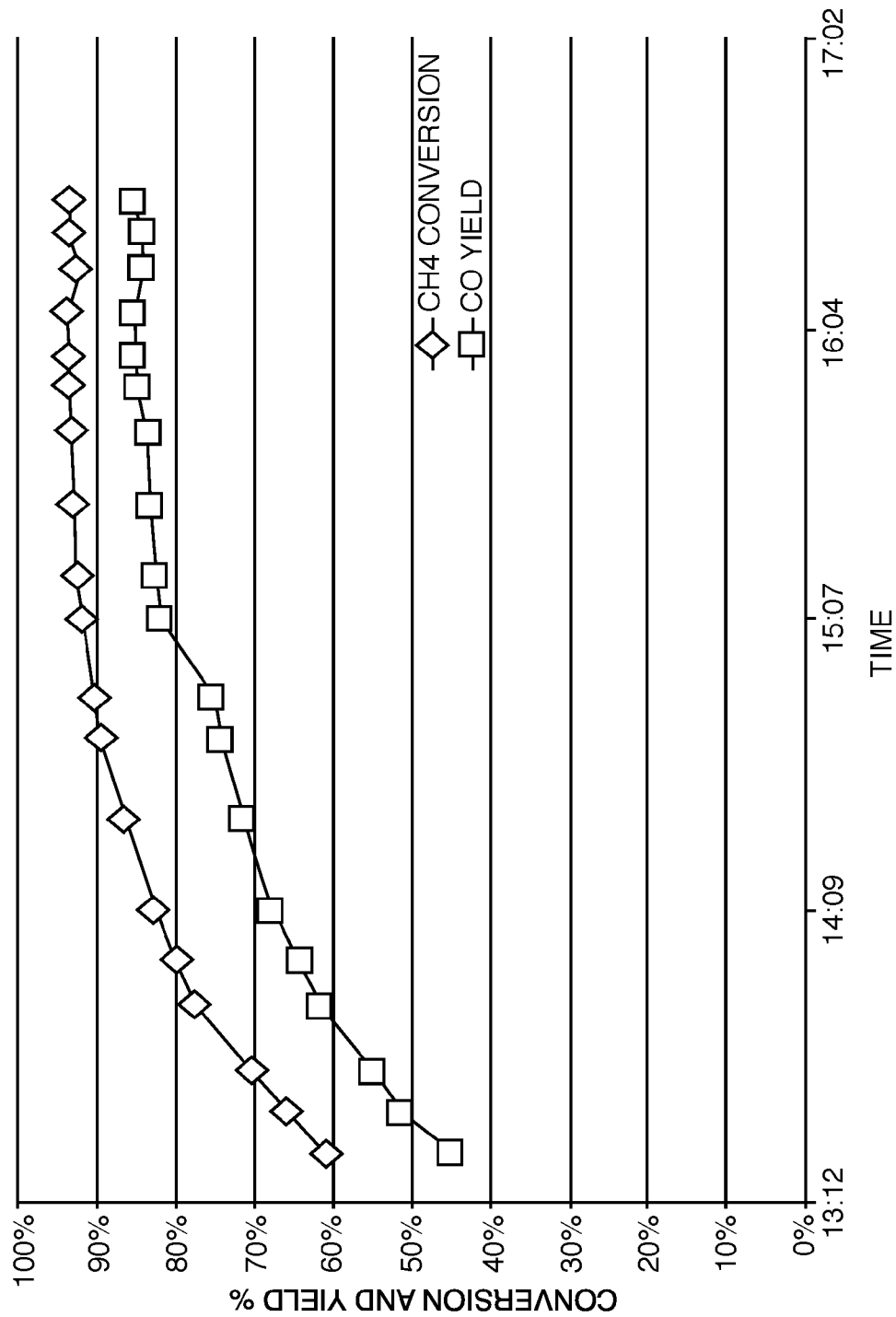
FIG. 8 shows data from one test of the DIEM pilot unit, showing performance of the DIEM pilot unit's reformer with air.

Calculated and measured results are remarkably close for space velocity corresponding to reforming of 300 SLM of methane with 900 SLM of air using 20 kg of catalyst, the conditions of the test. The time history of carbon monoxide yield and methane conversion from experimental data is shown in FIG. 8 for this representative test.

For preheating of methane and air streams, U-tube style heat exchangers were used. These heat exchangers were of 4 pass tube side and a single pass shell side construction. The inventors state that using true counter-flow heat exchangers with large surface area for gas preheating will improve performance of the reformer. Let's consider a case when air and methane are preheated to 700° C. instead of 400° C., while the exit temperature of the reformer is 750° C. Calculation shows that the CO yield improves to 94% and the dry gas composition from the reformer is as follows: Hydrogen: 39.4%, Carbon monoxide: 18.7%, Carbon dioxide: 0.8%, Methane: 0.03%, Nitrogen, argon: balance.

Calculation confirms than better reformer performance can be obtained when the gases are preheated to the maximum temperature which is the exit temperature of the reformer.

Performance of Pilot Unit Refomer with Oxygen-Enriched Air

Air contains approximately 20% oxygen with approximately 80% of nitrogen. The nitrogen component of air plays both positive and negative roles. On the positive side, nitrogen, being an inactive component with a significant heat capacity, moderates temperature extremes and reduces occurrences of hot spots. On the negative side, nitrogen dilutes carbon monoxide and hydrogen, reducing concentrations and partial pressures of these two gases. When partial pressures of hydrogen and carbon monoxide are decreased at the inlet of the DME synthesis reactor, two things happen: 1) maximum possible conversion to products decreases because equilibrium shifts away from products; and 2) the absolute reaction rates decreases with the decreasing concentration of the reactants.

Operation of the reformer with oxygen-enriched air was demonstrated. On a smaller scale, a flow of 240 SLM air enriched to 33% oxygen was demonstrated by passing compressed air through a gas separation membrane. For a larger scale pilot unit reformer tests, oxygen enriched air was made by adding pure oxygen to the air stream. This was done because not enough gas separation membranes were available for the large-scale tests. In one test, the reformer was operated with air enriched to oxygen concentration 28.5%-30%. CO yield of 89% was achieved and the following composition of dry gas out of the reformer was measured: Hydrogen: 36%, Carbon monoxide: 21.3%, Carbon dioxide: 1.8%, Methane: 0.8%, Nitrogen, argon: balance.

In this test, water was added to the reformer at approximately 1:4 water to methane mole ratio to prevent catalyst coking. Catalyst temperature was 860° C. on top of the catalyst bed and 720° C. at the exhaust. The flow of methane was approximately 300 SLM and 20 kg of reforming catalyst was used for this test.

This test was simulated assuming equilibrium is achieved in the reformer and the following numbers were calculated. The conversion of methane to CO was calculated to be 93% which compares well to the experimental conversion of 90%. The dry gas composition out of the reformer was calculated to be: Hydrogen: 44.4%, Carbon monoxide: 22.2%, Carbon dioxide: 1.1%, Methane: 0.6%, Nitrogen: balance.

Figure 9:
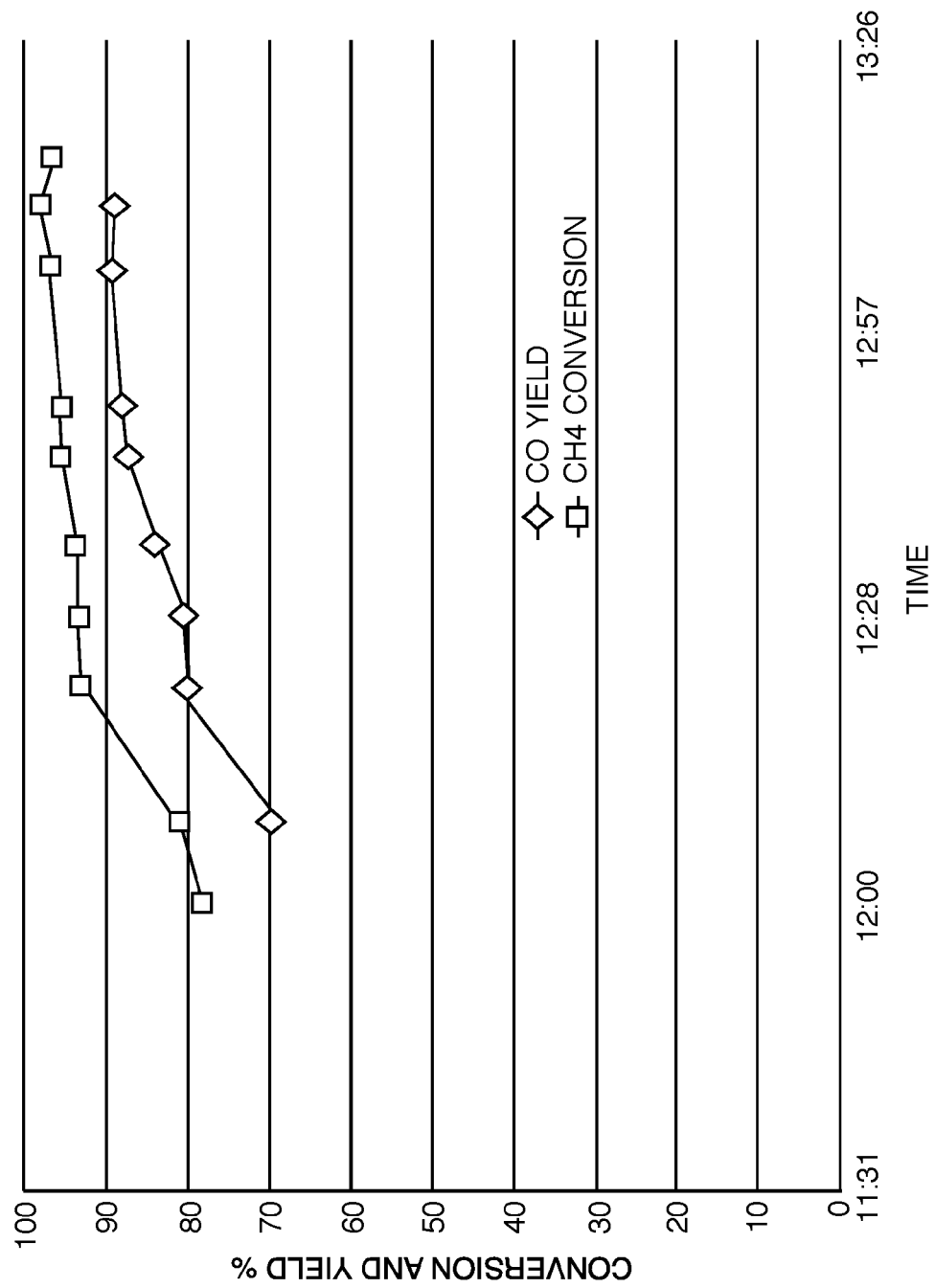
FIG. 9 shows data from another test of the DIEM pilot unit, showing performance of the DIEM pilot unit's reformer with oxygen-enriched air.

As in the case with unenriched air, a good agreement between the calculated and experimental results is observed. This indicates good performance of the air reforming unit. The time history of CO yield and methane conversion from experimental data are shown in FIG. 9 for this representative test (note symbols and legend for CO yield and methane conversion are reversed from the convention used in FIG. 8).

In another test, air enriched to approximately 40% oxygen was used. In this test, methane to water ratio was approximately 5:1, and the reformer exhaust temperature was approximately 750° C. The following dry gas composition was measured: Hydrogen: 46%, Carbon monoxide: 23%, Carbon dioxide: 3.1%, Methane: 5.4%, Nitrogen: balance.

The syngas obtained in this test, with high CO concentration (23%) and low inert gases concentration (31%), is well suited for synthesis of DME.

Syngas Recirculation

In the experiment conducted with air enriched to 30% oxygen, high temperature (860° C.) near the top of the catalyst bed was observed. The manufacturer of the catalyst does not recommend exceeding 900° C. for the catalyst, which is why tests with air enriched to oxygen concentration higher than 30% were not attempted.

It is advantageous to use higher oxygen concentrations in enriched air to reduce nitrogen content in the syngas for improved methanol yield. However, without sufficient nitrogen gas entering the reformer, the hot spot near the top of the catalyst bed will develop, which results in damage to the catalyst. The kinetics and thermodynamics of the reforming dictates that sufficient buffer gas needs to be present to prevent the catalyst from overheating. As shown below, this buffer gas can be recirculated syngas.

Equilibrium in reforming of methane at low pressures and high temperatures favors formation of carbon monoxide and hydrogen products. As long as equilibrium is favorable, part of the syngas can be recirculated to the reformer. This was investigated by performing equilibrium calculation for the case of air enriched to 45% oxygen. Membrane separation can produce air enriched to 45% oxygen, and membrane separation is one of the methods of oxygen enrichment which is suitable for field deployment at remote locations.

In the equilibrium calculation for air enriched to 45% oxygen concentration, 35% of the syngas is recirculated back to the reformer. The recirculated syngas is split after the condenser because at this point the syngas is cold and can be recirculated using a blower, which does not have to withstand high temperatures. The enriched air feed and methane are assumed to be preheated to 400° C., and the ratio of methane to water is set to 4:1. The ratio of enriched air to methane is varied to obtain reformer exit temperature of 750° C. For these conditions, the following composition of dry gases at the exit of the reformer is obtained: Hydrogen: 50%, Carbon monoxide: 23%, Carbon dioxide: 4%, Methane: 0.5%, Nitrogen: 22.5%. These results show that significant reduction of nitrogen concentration in the syngas can be achieved if air enriched with oxygen and syngas recirculation is used. If the recirculated syngas is counted as nitrogen, the effective oxygen concentration in the feed is only 19%, which is low enough to prevent formation of hot spots.

The above example is for air enriched to 45% oxygen. The reformer can be operated with air enriched to oxygen concentrations other than 45%, provided that sufficient syngas is recirculated to prevent catalyst overheating while achieving high yield of carbon monoxide from methane.

Synthesis of DME from Syngas

DME synthesis was demonstrated in multiple tests. Conversion efficiency of CO to DME varied with the reactor temperature, pressure, reformer gas composition, space velocity, catalyst composition, rector geometry, and other factors.

Figure 10:
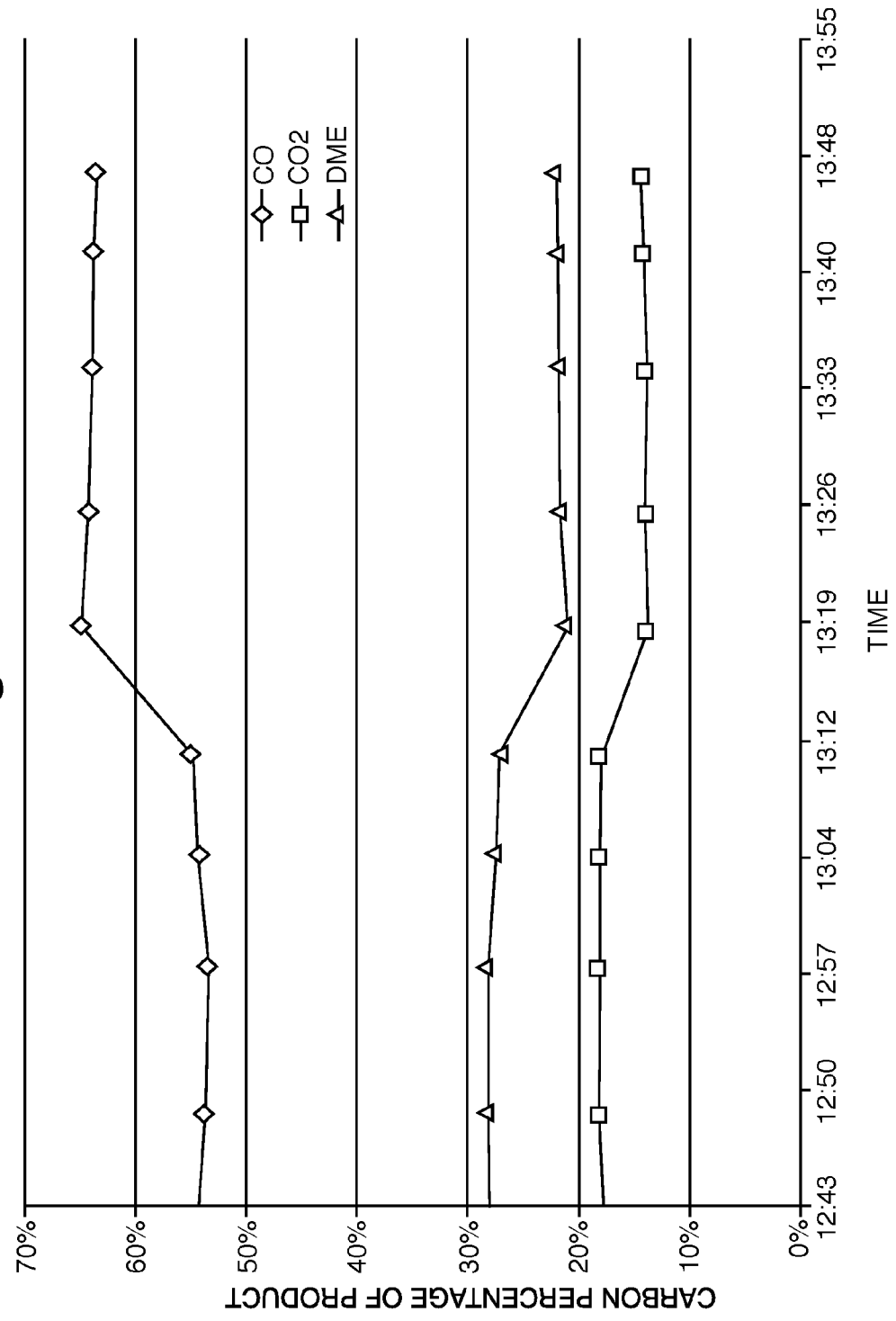
FIG. 10 shows data from yet another test of the DIEM pilot unit, showing performance of the DIEM pilot unit's synthesis of DME from syngas.

One example demonstrates DME synthesis from the reformer gas containing 18% CO at pressure of 600 psi. As shown in the above examples, syngas containing 16-21% CO can be made in the pilot system reformer. DME was synthesized using 60/40 weight/weight mixture of methanol catalyst and dehydration catalyst. The synthesis reactor was a jacketed 1.75-inch diameter tube holding approximately 2 kg of mixed catalyst. In the jacket, a heat transfer fluid (vegetable oil) was circulated to remove reaction energy. The gas entering the synthesis reactor had the following composition: 34% $H_2$, 18% CO and 48% $N_2$. Before entering the synthesis reactor, the reformer gas was preheated to a temperature of approximately 250° C. Catalyst temperature varied from 290° C. at the rector inlet to 240° C. at the reactor outlet. Conversion of approximately 50% were achieved at space velocity of 1200 vol/hr and conversion of 37% was achieved at space velocity of 1800 vol/hr. The time history of carbon conversion efficiencies from experimental data are shown on FIG. 10 for this representative test.

Equilibrium calculation shows that for conditions of the above test, 93% conversion of carbon monoxide to DME was possible.

Another example shows that for conditions of lower space velocity and higher CO concentration at the inlet, high CO conversion is observed. CO conversion of 76% was observed for space velocity of 700 vol/hr, reactor pressure 600 psi, and inlet hydrogen and carbon monoxide concentrations of 58% and 30%, respectively.

The above examples experimentally demonstrate that high CO conversion to DME is possible given sufficient residence time in the synthesis reactor.

DIEM System Advantages

By combining the catalysts, the system sends the methanol product directly on to be removed as DME in the same reactor. This lowers the total pressure require for efficient methanol conversion. That, in turn, allows the system to tolerate the presence of nitrogen, which otherwise would lower the partial pressure of the reactants too much. As a result, the system can use air instead of oxygen.

The system is using a special catalyst blend which works adequately well in the presence of $N_2$. In the baseline approach, for syngas generation, the catalyst is a Ni-based steam reforming catalyst. For DME synthesis, the catalyst is Cu—ZnO for methanol synthesis blended with gamma alumina for methanol dehydration to DME. The nitrogen (air) flow will influence the catalyst performance to the extent of lowering the partial pressures of the product constituents and increasing reactor size. This can be mitigated by oxygen enrichment of the air stream into the syngas generator. Some downstream benefits of oxygen enriched air (OEA) include reactant flow rate reduction, reduced air/NG preheater size (heat exchanger), enhanced partial pressure of CO and $H_2$, and lower pressure operation.

Stream 20 is 98% pure DME—there is very little water and methanol. The system is using a single-step syngas-to-DME catalyst. The mole fractions of water and methanol are on the order of 0.005, where the amount of methanol generated in the DME reactor can be tailored by the loading of gamma alumina. There are two nominal solvent conditions for the absorber/stripper. One is water at 0° C. and 20 bar, and the other is 30% methanol in water at 20° C. and 20 bar. In some embodiments, the methanol and water concentration would build up in the system, so a bleed/recovery stream may be needed to accommodate the excess (not shown in FIG. 1).

Since the DIEM works without oxygen separation and without steam production, these are unique characteristics for this type of conversion. The inventors have developed a unique process using a blend of catalysts that can operate under these conditions, making the overall process simple, enabling the radical simplification necessary for field-deployment.

One key challenge is to avoid coking. Steam suppresses coking, but the system does this without steam. The inventors have found that if the system can operate in a regime above 700° C., coking can be prevented. The challenge is to keep the reaction always above 700° C. Also, operating with air (without pure oxygen), effective heat exchange is needed to pre-heat the air and methane—otherwise, the temperature does not get high enough. This is done in a one pass system to ensure simplicity. No oxygen production subsystems or steam boilers are needed.

Unlike a typical system that is high pressure and high temperature, the part of the system that is hot is operating near atmospheric pressure: the front half of the system is 800° C., but below 15 psi; in the part of the system that is high-pressure (300 psi), the temperatures are below 250° C., which does not challenge steel.

In short, the system and process are unique. It is a combined methanol/DME reactor, but operates under conditions in which neither methanol nor dimethyl ether is currently produced, and is controlled as an integrated system. This system would be most desirable as a fully-automated, remotely controlled, mobile system that can be taken directly to where stranded wells are located. It is designed for mobile, medium-scale installation, which can be economically practical because of its radical simplicity and because it has freed itself from the requirements of oxygen and steam. The system is readily controllable in a small-scale system, and fully automated to lessen the labor burden. The inventors are not going after economies of scale, but economies of mass-production, to produce a standardized system that uses very little labor to control and operate. The system does not need any external utilities, as the hydrogen produced is more than sufficient to run the unit.

In short, the inventors have developed a mobile system that goes from flare gas of any composition—wet or dry—directly to DME—without needing oxygen or steam.

Economic Estimates

One of many illustrative scenarios is presented here to demonstrate the potential profitability of the DIEM system. In this scenario, dry methane gas is assumed to be the feedstock. Other configurations and use cases are also possible. This economic analysis is illustrative of the invention only and is not meant to limit the scope of the present invention.

For the system size in Table 1, the value of the DME product is about $3,000 per day, or $1,095,000 per year. If it is using flare gas for feedstock, the cost of feedstock is essentially zero. If using commercial natural gas priced at $4 per MCF, the cost of feedstock is $672/day, or $245,000/year. If the unit is sold with a 6-year lease at 5% interest, the capital cost of the unit will be about $347,000 per year for the first six years, and essentially zero afterwards. Two full-time worker-equivalents, priced at $100,000 per year each, would be sufficient to operate the machine. Four cases are defined by whether the unit is operating during the first six years, or afterwards, and whether the unit is using flare gas or commercial gas. These are examined in Table 2 as cases A, B, C, and D, respectively.

TABLE 2

Economic Estimates of the DIMES Unit

| Feedstock | Case A Flare Gas | Case B Flare Gas | Case C Commercial Gas | Case D Commercial Gas |
| --- | --- | --- | --- | --- |
| Period of Ops. | First 6 years | After 6 years | First 6 years | After 6 years |
| Annual Revenue | $1,095,000 | $1,095,000 | $1,095,000 | $1,095,000 |
| Capital Cost/yr | $347,000 | $0 | $347,000 | $0 |
| Feedstock Cost/yr | $0 | $0 | $245,000 | $245,000 |
| Labor Cost/yr | $200,000 | $200,000 | $200,000 | $200,000 |
| Net Profit/yr | $548,000 | $895,000 | $303,000 | $650,000 |

Therefore, the company that manufactures the machine can make a three to one profit on each unit sold, while allowing the user to profit substantially starting on the very first day of operation, with profits growing substantially after six years when the machine is paid off However, Table 2 limits consideration of the value of the DIEM unit to the value of the DME product itself. In fact, in many cases there will be an additional value proposition, which may be substantially larger. This is because in many cases, those producing flare gas will be oil companies, whose wells may be shut down if their flaring is not eliminated. The value lost by losing oil production in this way may be an order of magnitude greater than the value of the DME itself. For example, the inventors are acquainted with one oil producer who is currently flaring about 168 MCF of natural gas, who is being threatened with shutdown for this reason. If this occurs, the operator will lose its oil revenue, which could be millions per year. Thus, the value of the DIEM to such an operator could be many times greater than the numbers in Table 2, taken in isolation, would indicate.

On a per-unit basis, the DIEM system would be capable of manufacturing DME at a cost of $1.04/gallon ($0.41/kg) DME during the first 6 years, and at a price of $0.38/gallon ($0.15/kg) DME thereafter (after all the capital costs have been paid back). This corresponds to a DME cost of about $0.71/gallon ($0.28/kg) DME amortized over 12 years. This corresponds to a cost of $1.07 per Diesel-Gallon-Equivalent (DGE) amortized over 12 years, which is highly competitive with historical diesel prices, even during depressed oil price conditions.

Sulfur Removal Subsystem Embodiments

If necessary, and in some embodiments, as shown in FIG. 1, a desulfurization subsystem can be added to remove any sulfur from the raw gas stream. The desulfurization subsystem would be applied to the gas stream upstream of the entire DIEM process. Several alternative sulfur treatment and removal methods are possible according to various embodiments of the present invention. Dry sorbents may be used to capture sulfur in the feed gas. Calcium oxide, magnesium oxide, and sodium carbonate are example dry sorbents that are capable of trapping sulfur gases in solid form (as sulfates or sulfites, depending on the relative oxidation conditions). A fine sorbent can be injected into the feed gas, with resulting sulfur-containing solids then collected. In other embodiments, sulfur may also be removed by using a wet scrubber subsystem. Wet scrubbers can be configured in venturi, packed-column, or tray-type systems in which the feed gas is contacted with a scrubbing solution or slurry. The resulting scrubber solution or slurry must then be disposed.

That is, for sour flare gas that is rich in $H_2S$, the raw gas can be cleaned in a unit before further processing. For sulfur concentrations less than about 500 ppm, a disposable, solid iron-based sorbent would be optimal (low capital costs). The solid sorbent produces a recyclable iron sulfide waste. For higher sulfur concentrations, a liquid-based iron-chelate process would be appropriate. The liquid iron-chelate process produces an elemental sulfur filter cake by-product. Either by-product can be recycled or disposed off-site.

Modular System Design

The present invention may also be configured as a modular system, which may be created from modular units (for example, but not limited to, 170 mcf units). Each unit can run in parallel autonomously without interference. These units may be combined at the field depending on the application, and the requirements of a given user. Depending on the gas processing needs of a particular site, multiple units may be combined to provide the necessary processing power. Similarly, as production declines or gas gathering lines are added, units can be removed and moved to new production locations.

Various Use Cases of the Present Invention

Several alternative use cases of the present invention are now presented. These use cases are illustrative of the possible applications of the present invention and are not meant to be exhaustive or limiting.

Figure 11:
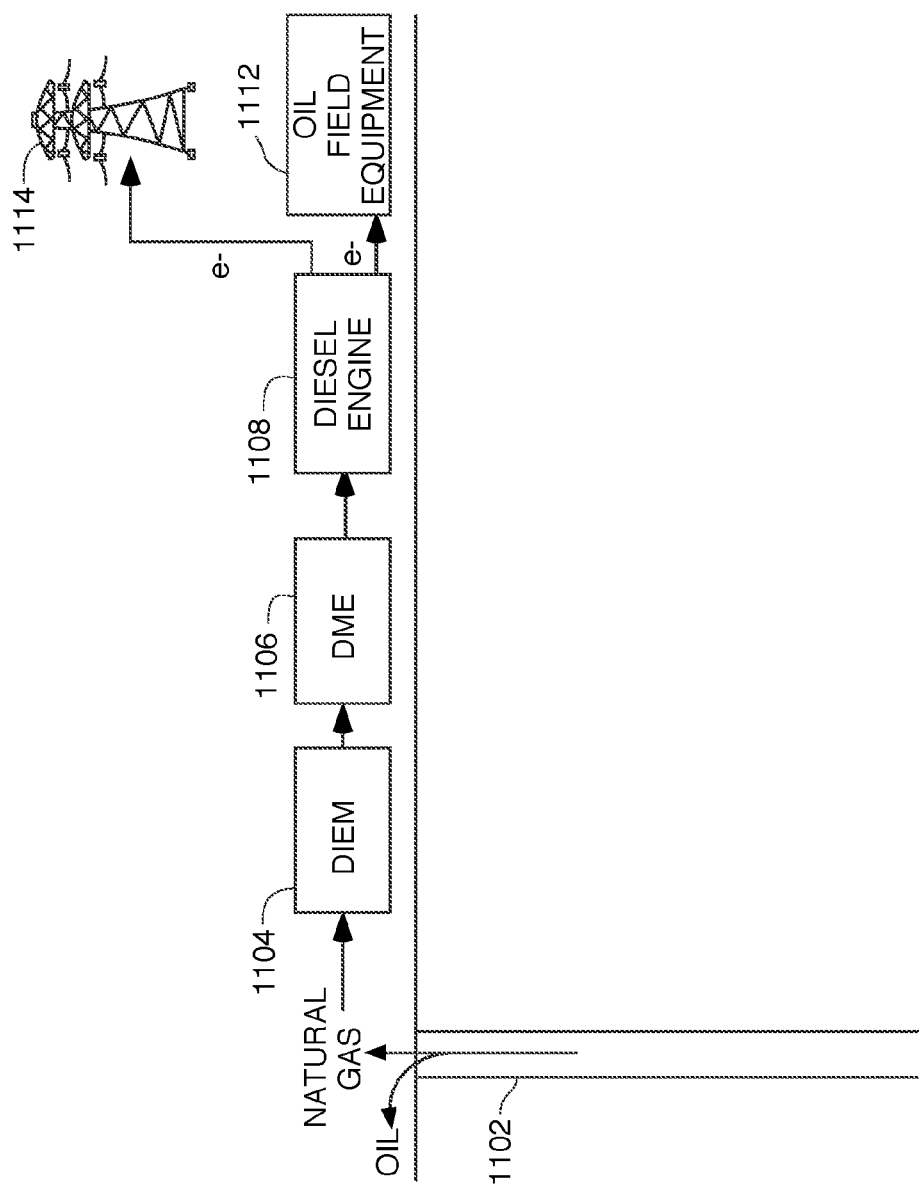
FIG. 11 illustrates an example use case of the DIEM in which a portion of the DME stream is used in on-site diesel engines.

FIG. 11 illustrates an example of a use case of the DIEM in which a portion of the DME stream is used in on-site diesel engines. As shown, oil and associated gas (which is normally flared) is produced from well 1102, which may be a well fracked with hydraulic fracturing as practiced in North Dakota. The flare gas is taken to DIEM unit 1104, where it is turned into DME 1106, a portion of which can be utilized to power an engine/electric generator combo 1108. The produced electricity may be used on-site to power various oil field equipment 1112, or transmitted to the grid 1114.

Figure 12:
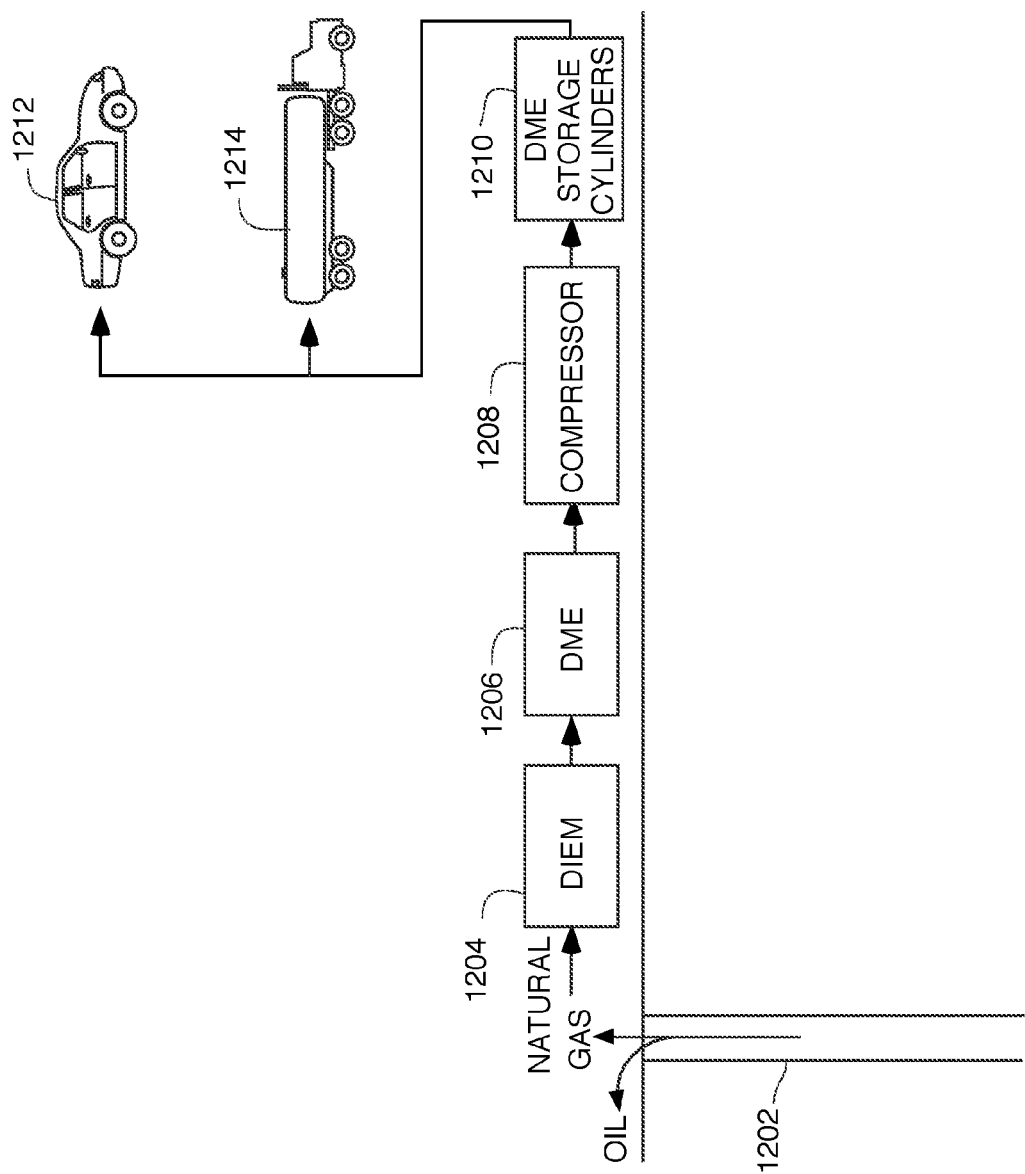
FIG. 12 illustrates another example use case of the DIEM in which a portion of the DME stream is transported as diesel fuel.

FIG. 12 illustrates another example of a use case of the DIEM in which a portion of the DME stream is used as diesel fuel or transported to a remote location to power remote diesel gensets. As shown, oil and associated gas (which is normally flared) is produced from well 1202. The flare gas is taken to DIEM unit 1204, where it is turned into DME 1206, a portion of which can be compressed with compressor 1208 to fill DME storage cylinders 1210. The stored DME may be off-loaded directly to DME-enabled vehicle tanks 1212 for use in diesel vehicles, or loaded into DME-enabled transport tankers 1214, which may be transported to remote locations (for example, to fuel diesel fleets or provide diesel fuel to drilling rigs).

Figure 13:
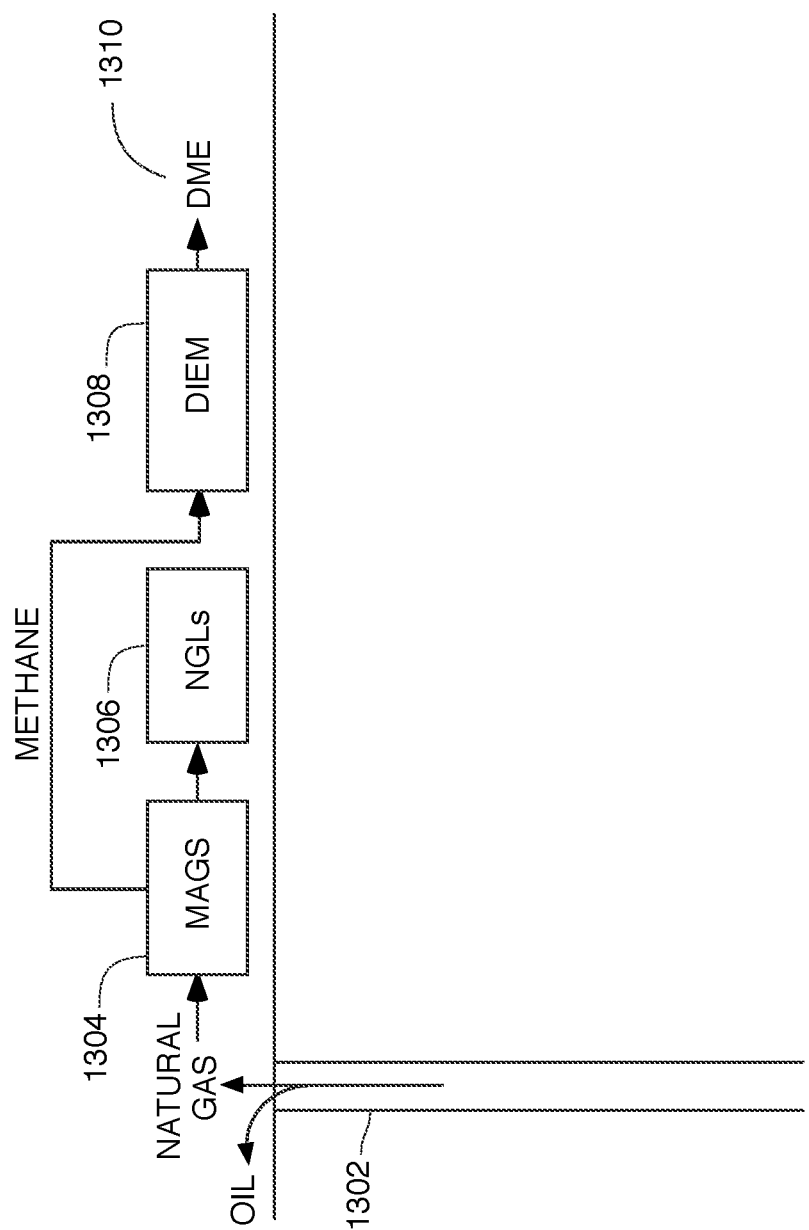
FIG. 13 illustrates yet another example of a use case of the DIEM.

FIG. 13 illustrates yet another example of a use case of the DIEM in which the DIEM is used in conjunction with the mobile alkane gas separator (MAGS), which is another product of the Applicant of this invention, in which the NGLs are first removed from wet flare gas, and the remaining dry $CH_4$ stream is converted to DME for easy transport. As shown, oil and associated gas (which is normally flared) is produced from well 1302. The flare gas is first taken to MAGS unit 1304, where it is separated into NGLs 1306 and lean methane. The methane may then be upgraded to DME 1310 via DIEM unit 1308. The DME 1310 may be collected on-site in storage containers and transported from the oil site using truck-trailers in the same manner as the oil is transported from the site. One advantage of the embodiment shown here is that the NGLs and DME produced can be more easily transported from the oil site than the original raw natural gas stream. Since the DIEM unit can run on any flare gas whatsoever—wet or dry—the use of the MAGS as shown here is optional in cases where NGLs are desired to be separated before DME is manufactured from the remaining methane stream for any reason.

Potential Macro-Environmental and Macroeconomic Impact

Previously, the impact of the technology on a single user was discussed, to show that it would be highly profitable. This is the key to the propagation of the technology to many fields. In this section, the macro-environmental and macroeconomic effect of the technology is discussed once it has been put into broad use, showing that it could have a major impact in both increasing stranded gas utilization, meeting expanded electricity needs of drillers, and reducing carbon emissions.

In early 2014, in North Dakota alone, 340,000 mcf per day (340 mmcf/day or 340 million cubic feet per day) of natural gas was being flared, approximately 60% of which is coming from wells producing 200 mcf per day or more each (Source: Wocken, C. A.; Stevens, B. G.; Almlie, J. C.; Schlasner, S. M., *End-Use Technology Study—An Assessment of Alternative Uses for Associated Gas*, National Energy Technology Laboratory, Pittsburgh, Pa., April 2013). In 2011, the entire U.S. oil and gas industry annually flared approximately 7.1 billion cubic meters (bcm), or 250 billion cubic feet (bcf). If 20% of this flaring was avoided using DIEM, then ~2.8 Mt of $CO_2$-equivalents would be avoided per year in the U.S. This represents not just a significant environmental benefit, but a significant economic opportunity for the country.

Meanwhile, it is estimated that in 2011, Canada flared 2.4 billion $m^3$ per year (Source: Global Gas Flaring Reduction Partnership, *Estimated Flared Volumes from Satellite Data, 2007-2011*, 2013.) If 45% of this flaring was avoided using DIEM in Canada (Canada's flare sites are more concentrated), then an additional ~2 Mt of $CO_2$-equivalents would be avoided per year in Canada. This represents not just a significant environmental benefit, but a significant economic opportunity for Canada as well.

As in the U.S. and Canada, the rest of the world is also seeing a great increase in flaring in recent years (Source: Global Gas Flaring Reduction Partnership, *Estimated Flared Volumes from Satellite Data, 2007-2011*, 2013.) Using the DIEM, the entire world could achieve greater energy abundance and simultaneously reducing greenhouse gas emissions from the worldwide oil and gas sector.

Long-Felt, Unsolved Need for Cost-Effective, on-Site Gas Capture

As stated by a recent government-commissioned study, around 34% of North Dakota's produced associated gas is flared, nearly 340 million cubic feet per day (340 mmcf/day) in 2014, nearly double the 2011 flaring estimates of 190 million cubic feet per day (190 mmcf/day). (Source: Wocken, C. A.; Stevens, B. G.; Almlie, J. C.; Schlasner, S. M., *End-Use Technology Study—An Assessment of Alternative Uses for Associated Gas*, National Energy Technology Laboratory, Pittsburgh, Pa., April 2013, incorporated by reference in its entirety herein.) This U.S. Department of Energy study demonstrates the long-felt and unsolved need for mobile technology to address this issue. This study also shows that no existing technology can produce a useable and transportable liquid stream from raw flare gas, wet or dry, which is one innovative aspect of the present invention. This discussion is merely illustrative and exemplary, and is not intended to limit the scope of the present invention or its application or uses.

Several random samples of Bakken region wellhead gas quality data are presented in Table 3 (Source: Wocken, C. A.; Stevens, B. G.; Almlie, J. C.; Schlasner, S. M., *End-Use Technology Study—An Assessment of Alternative Uses for Associated Gas*, National Energy Technology Laboratory, Pittsburgh, Pa., April 2013). This high NGLs content typically corresponds with high Wobbe index (higher energy content of 1300-2000 BTU/cf) when compared to residential pipeline gas (~1000 BTU/cf). All of these can be converted to DME directly, or after separation of the higher carbon components from methane, with the methane converted to DME.

TABLE 3

Selected Flare Gas Data from Wellheads in the Bakken Formation

| Wellhead Sample: | Sample 1 | Sample 2 | Sample 3 |
|---|---|---|---|
| Methane, mol % | 70.23 | 48.07 | 73.93 |
| Ethane, mol % | 13.94 | 18.78 | 13.25 |
| Propane, mol % | 6.7 | 14.87 | 5.55 |
| Butane+ (C4+), mol % | 5.5 | 16.38 | 4.32 |
| $CO_2 + N_2$, mol % | 3.44 | 1.72 | 2.87 |
| $H_2S$ | 0.19 | 0.18 | 0.08 |
| Wobbe Index, BTU/scf | 1470 | 1712 | 1454 |
| Methane No. (MN) | 53.2 | 43.5 | 56.1 |

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

What is claimed is:

1. A method for converting a raw natural gas into dimethyl ether (DME) using air as a source of oxygen, comprising:
generating syngas in an air reformer from a feedstock comprising the raw natural gas and the air, wherein the syngas comprises carbon monoxide, hydrogen, and nitrogen from the air;
compressing the syngas that comprises the carbon monoxide, the hydrogen, and the nitrogen;
synthesizing a DME mixture from the syngas in a single reaction chamber using a mixed catalyst bed; and
purifying the DME mixture to produce a purified DME stream, wherein essentially all carbon in the purified DME stream comes from the raw natural gas, and wherein unreacted nitrogen from the DME mixture is returned to atmosphere.

2. The method of claim 1, further comprising:
removing sulfur from the raw natural gas.

3. The method of claim 1, wherein the mixed catalyst bed comprises a syngas-to-methanol synthesis catalyst and a methanol-to-DME dehydration catalyst.

4. The method of claim 3, wherein the syngas-to-methanol synthesis catalyst is Cu—ZnO.

5. The method of claim 3, wherein the methanol-to-DME dehydration catalyst is gamma alumina.

6. The method of claim 1, wherein the mixed catalyst bed comprises Cu—ZnO for methanol synthesis blended with gamma alumina for methanol dehydration to DME.

7. The method of claim 1, wherein the purifying step utilizes an absorber column comprising an aqueous solvent for absorbing the DME, while effluent gases ($N_2$, $H_2$, CO, and $CO_2$) are exhausted.

8. The method of claim 7, wherein the effluent gases are combusted to provide power to the compressing step.

9. The method of claim 7, wherein the purifying step further utilizes a stripper column, wherein DME-rich solvent solution is sent to the stripper column, and wherein the purified DME stream is distilled from the aqueous solvent, and a resulting lean solvent is recycled back to the absorber column.

10. The method of claim 1, wherein the generating step comprises reforming the raw natural gas and the air in a presence of a steam reforming catalyst in the air reformer.

11. The method of claim 10, wherein air enriched in oxygen is used to increase concentrations of hydrogen and carbon monoxide in the syngas.

12. The method of claim 11, wherein up to 40% air enrichment is utilized, eliminating a need for a large oxygen production system.

13. The method of claim 10, wherein water is added to the air reformer to prevent catalyst coking.

14. The method of claim 13, wherein the water is recycled to the air reformer from a condenser downstream from an air recycling unit.

15. The method of claim 13, wherein a water addition rate is controlled to minimize conversion of carbon monoxide to carbon dioxide.

16. The method of claim 13, wherein distilled water is converted to steam inside the air reformer.

17. The method of claim 1, wherein gases in the air reformer are well mixed before the air reformer's catalyst bed to improve the air reformer's performance, wherein a gas mixer mixes the raw natural gas and the air before these gases pass through the air reformer's catalyst bed.

18. The method of claim 1, wherein some of the syngas is recirculated back to the air reformer to prevent hot spots in the mixed catalyst bed.

19. The method of claim 1, wherein the natural gas and the air are preheated to improve carbon monoxide yield.

20. The method of claim 1, wherein the air reformer operates at a high-temperature but low pressure, whereas the single reaction chamber operates at high pressure but low temperature.

21. The method of claim 20, wherein a temperature of the air reformer is above 700° C. (973 K) at atmospheric pressure (1 bar).

22. The method of claim 20, wherein a temperature of the single reaction chamber is below 400° C. (673 K) at a pressure between 100 and 2,000 psi (6-140 bar).

23. The method of claim 1, wherein an in-reactor cooling system with a water coolant is used to reject heat and control DME reactor isotherms in the single reaction chamber.

24. The method of claim 23, wherein the water coolant is converted to high temperature, high pressure steam and used in a reboiler to purify the DME mixture in a stripper column.

* * * * *